(12) United States Patent
Nielsen, Jr.

(10) Patent No.: US 11,963,991 B2
(45) Date of Patent: *Apr. 23, 2024

(54) TREATMENT OF WARTS

(71) Applicant: Nielsen BioSciences, Inc., San Diego, CA (US)

(72) Inventor: H. Stewart Nielsen, Jr., San Diego, CA (US)

(73) Assignee: Nielsen BioSciences, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/304,629

(22) Filed: Apr. 21, 2023

(65) Prior Publication Data

US 2023/0256042 A1   Aug. 17, 2023

Related U.S. Application Data

(60) Continuation of application No. 17/378,411, filed on Jul. 16, 2021, now Pat. No. 11,666,617, which is a division of application No. 16/532,247, filed on Aug. 5, 2019, now Pat. No. 11,116,808.

(60) Provisional application No. 62/880,742, filed on Jul. 31, 2019, provisional application No. 62/714,942, filed on Aug. 6, 2018.

(51) Int. Cl.
*A61K 36/064*   (2006.01)
*A61K 9/00*   (2006.01)
*A61P 17/12*   (2006.01)

(52) U.S. Cl.
CPC .......... *A61K 36/064* (2013.01); *A61K 9/0019* (2013.01); *A61P 17/12* (2018.01)

(58) Field of Classification Search
None
See application file for complete search history.

(56) References Cited

U.S. PATENT DOCUMENTS

| | | | |
|---|---|---|---|
| 5,614,538 | A | 3/1997 | Nelson et al. |
| 6,270,781 | B1 | 8/2001 | Gehlsen |
| 6,350,451 | B1 | 2/2002 | Horn et al. |
| 6,797,491 | B2 | 9/2004 | Neefe et al. |
| 2002/0142005 | A1 | 10/2002 | Horn et al. |
| 2005/0175634 | A1 | 8/2005 | Horn et al. |
| 2012/0171241 | A1 | 7/2012 | Bardotti et al. |
| 2013/0251741 | A1 | 9/2013 | Pietersz |

FOREIGN PATENT DOCUMENTS

| | | |
|---|---|---|
| CN | 1168653 A | 12/1997 |
| CN | 1342076 A | 3/2002 |
| CN | 1678344 A | 10/2005 |
| CN | 101914458 A | 12/2010 |
| CN | 104703601 A | 6/2015 |
| WO | WO 2014/008248 A2 | 1/2014 |
| WO | WO 2015/054678 | 4/2015 |

OTHER PUBLICATIONS

Package Insert for CANDIN package insert 1995 (hereinafter "CANDIN"). www.fda.gov/media/97965/download 5 pages.*
Abd-Elazeim et al., "Evaluation of IL-12 Serum Level in Patients with Recalcitrant Multiple Common Warts, Treated by Intralesional Tuberculin Antigen," *J. Dermatological Treatment*, 25:264-267 (2014).
Abdelmaksoud, "Reply to Significance of Interferon Gamma in the Prediction of Successful Therapy of Common Warts by Intralesional injection of Candida Antigen," *Intl. J. Dermatology*, 56:1505-1506 (2017).
Aldahan et al., "Efficacy of Intralesional Immunotherapy for the Treatment of Warts: A Review of the Literature," *Dermatologic Therapy*, 29:197-207 (2016).
Alikhan et al., "Use of Candida antigen injections for the treatment of verruca vulgaris: A two-year Mayo Clinic experience," *Journal of Dermatological Treatment*, 27(4):355-358 (2015).
Allen et al., "What's New in Human Papillomavirus Infection," *Curr. Opin. Pediatrics*, 12:365-369 (2000).
Ampel et al., "An archived lot of coccidioidin induces specific coccidioidal delayed-type hypersensitivity and correlates with in vitro assays of coccidioidal cellular immune response," *Mycopathologia*, 161:67-72 (2006).
Ampel et al., "An Analysis of Skin Test Responses to Spherulin-Based Coccidioidin (Spherusol®) Among a Group of Subjects with Various Forms of Active Coccidioidomycosis," *Mycopathologia* 184:533-538 (2019).
Anderes et al., "The lipids of an auxutrophic avirulent mutant of *Coccidioides immitis*," *Sabouraudia*, 11(2):149-157 (1973).
Ashman et al., "IL-12 and Related Cytokines: Function and Regulatoly Implications in *Candida albicans* Infection," *Clinical and Developmental Immunology*, 2011(686597):1-10 (2010).
Aung et al., "Intralesional Injection," Downloaded from Https[colon]dermnetnz [dot\org/topics/introlesional-injection/ (2020).
Bavinck et al., "Treatments for Common and Plantar Warts," *BMJ*, 342:d3119 (2011).
Borchers et al., "The Immune Response in *Coccidioidomycosis*," *Autoimmunity Reviews*, 10:94-102 (2010).
Burkhart, "*Propionibacterium acnes*: An Indigenous Bacterium May be Pathogenic in Several Cutaneous Disease States," *Arch. Dermatol.*, 137:1250-1255 (2001).
Campbell et al., "A Systematic Review on TST and IGRA Tests Used for Diagnosis of LTBI in Immigrants," *Mol. Diagn. Ther.*, 19:9-24 (2015).

(Continued)

*Primary Examiner* — Oluwatosin A Ogunbiyi
(74) *Attorney, Agent, or Firm* — Arnold & Porter Kaye Scholer LLP

(57) ABSTRACT

Disclosed herein are compositions having standardized potencies for use in the treatment of warts. Methods of treating a common wart comprising administering one or more intralesional injections of compositions having standardized potencies to a patient in need thereof are also disclosed. Further disclosed are methods of treating a non-common wart administering one or more intralesional injections of compositions having standardized potencies to a patient in need thereof.

20 Claims, 5 Drawing Sheets

(56) References Cited

OTHER PUBLICATIONS

Cengiz et al., "Effectiveness and Safety Profile of 40% Trichloroacetic Acid and Clyotherapy for Plantar Warts," *J. Dermatol.*, 43(9):1059-1061 (2016).
Ciconte et al., "Warts are not merely blemishes on the skin: A study on the morbidity associated with having viral cutaneous warts," *Australasian Journal of Dermatology*, 44:169-173 (2003).
Clifton et al., "Immunotherapy for Recalcitrant Warts in Children Using Intralesional Mumps or *Candida* Antigens," *Pediatric Dermatology*, 20(3):268-271 (2003).
Converse, "Growth of Spherules of *Coccidioides immitis* in a Chemically Defined Liquid Medium," *Proc. Soc. Exp. Biol. Med.*, 90(3):709-711 (1955).
Crawford et al., "Which risk factors and signs and symptoms are associated with coccidioidomycosis?" *The Journal of Family Practice*, 63(12):747, 756 (2014).
Dall'Oglio et al., Treatment of Cutaneous Warts, *Am. J. Clin. Dermatol.*, 13(2):74-96 (2012).
Dasher et al., "Immunotherapy for Childhood Warts," *Pediatr. Ann.*, 38(7):373-379 (2009).
Davies et al., "Clinical Usefulness of Skin Testing in Histoplasmosis, Coccidioidomycosis, and Blastomycosis," *Am. Rev. Respir. Dis.*, 138:1081-1082 (1988).
Deresinski et al., "Spherulin Skin Testing and Histoplasmal and Coccidioidal Serology: Lack of Effect," *Am. Rev. Respir. Dis.*, 116:1116-1118 (1977).
Edwards, et al., "Prevalence of Sensitivity to Coccidioidin, with Special Reference to Specific and Nonspecific Reactions to Coccidioidin and to Histoplasmin," *Sensitivity to Coccidioidin*, vol. XXXI, pp. 35-60 (1957).
Enns et al., "Intralesional Immunotherapy with *Candida* Antigen for the Treatment of Molluscum Contagiosum in Children," *Pediatric Dermatology*, 28(3):254-258 (2011).
Extended European Search Report issued on Jun. 13, 2022 in European Appln. 19846461.2.
Feldstein et al., "Successful Medical Treatment of a Severe Reaction to Red Tattoo Pigment," *Journal of Drugs in Dermatology*, 13(10):1274-1275 (2014).
Furue et al., "Prevalence of dermatological disorders in Japan: A nationwide, cross-sectional, seasonal, multicenter, hospital-based study," *Journal of Dermatology*, 38:310-320 (2011).
Galgiani et al., "Coccidioidomycosis," *Treatment Guidelines for Coccidioidomycosis*, 41:1217-1223 (2005).
Garza et al., "Intralesional *Candida* Antigen Immunotherapy for the Treatment of Recalcitrant and Multiple Warts in Children," *Pediatric Dermatology*, 32(6):797-801 (2015).
Gerlero et al., "Actualización sobre el tratamiento de las verrugas vulgares en los niños," *Actas Dermosifiliogr.*, 107(7):551-558 (2016).
Gordon et al., "Delayed Cutaneous Hypersensitivity in Normals: Choice of Antigens and Comparison to in vitro Assays of Cell-Mediated Immunity," *J. Allergy Clin. Immunol.*, 72:487-494 (1983).
Haga et al. [Abdelmaksoud], "Reply to Significance of Interferon Gamma in the Prediction of Successful Therapy of Common Warts by Intralesional Injection of *Candida* Antigen," *Intl. J. Dermatology*, 56:1505-1506 (2017).
Haller, "*Candida* Antigen Injection Proves Effective Treatment for Warts," *Am. Fam. Physician*, 61(2):478-480 (2000).
Harada, "Clinical Application of Fungus Extracts and its Culture Filtrate in the Treatment of Skin Diseases: (3) *Candida* Vaccine in the Treatment of Warts," *Japanese Journal of Dermatology*, 89(6):397-402 (1979).
Hasenclever et al., "Antigenic Studies of *Candida*," *Journal of Bacteriology*, 82:578-581 (1961).
Hendriksen, "Validation of Tests Methods in the Quality of Control of Biologicals," *Dev. Biol. Stand. Basel*, 101:217-221 (1999).
Heymann, "Yeast Rising: Predicting the Efficacy of *Candida* Antigen Immunotherapy for Warts," *Dermatology World*, retrieved from the internet at www[dot]aad[dot]org/dw/dw-insights-and-inquiries/medical-dermatology/yeast-rising-predicting-the-efficacy-of-candida-antigen-immunotherapy-for-warts; pp. 1-5 (2017).
Ho et al., "Diagnosis and Initial Management of Musculoskeletal Coccidioidomycosis in Children," *J. Pediatr. Orthop.*, 34(5):571-577 (2014).
Horn et al., "Intralesional Immunotherapy of Warts with Mumps, *Candida*, and *Trichophyton* Skin Test Antigens," *Arch. Dermatol.*, 141:589-594 (2005).
Huckabone et al., "Coccidioidomycosis and Other Systemic Mycoses of Marine Mammals Stranding along the Central California, USA Coast: 1998-2012," *Journal of Wildlife Diseases*, 51(2):295-308 (2015).
"Injections, Intralesional" http://id[dot]nlm[dot]nih[dot]gov/mesh/D015552 retried Jan. 11, 2021.
Isoda, "Pathological observations in experimental *Candida* infection of sensitized guinea pigs," *Mycopathologia*, 91:187-192 (1985).
Johnson et al., Intralesional Injection of Mumps or *Candida* Skin Test Antigens: A Novel Immunotherapy for Warts, *Arch. Dermatol.*, 137:451-455 (2001).
Johnson et al., "A Reformulated Spherule-Derived Coccidioidin (Spherusol) to Detect Delayed-Type Hypersensitivity in Coccidioidomycosis," *Mycopathologia*, 174:353-358 (2012).
Kabe et al., "Antigenicity of fractions from extracts of *Candida albicans*. The immediate and delayed-type respiratory responses in guinea pigs," *J. Allergy*, 47(2):59-75 (1971).
Kafka et al., "Disseminated Coccidioidomycosis in Children," *The Journal of Pediatrics*, 98(3):355-361 (1981).
Kashem et al., "Skin Immunity to *Candida albicans*," *Trends in Immunology*, 37(7):440-450 (2016).
Khozeimeh et al., "Intralesional Immunotherapy Compared to Cryotherapy in the Treatment of Warts," *Intl. J. Dermatology*, 56:474-478 (2017).
Khurshid et al., "Role of *Candida* antigen in treatment of viral warts: a placebo-controlled study," *Journal of Pakistan Association of Dermatologists*, 19:146-150 (2009).
Kim et al., "Phase 1 Clinical Trial of Intralesional Injection of *Candida* Antigen for the Treatment of Warts," *Arch. Dermatol.*, 146(12):1431-1433 (2010).
Klotz et al., "Systemic Anaphylaxis Immediately Following Delayed Hypersensitivity Skin Tests," *Annals of Allergy*, 49(3):142-145 (1982).
Kollman et al., "Regression of Nevi after *Candida* Injection for the Treatment of Verruca Vulgaris," *Pediatric Dermatology*, 34(2):199-200 (2017).
Kwok et al., "Topical Treatments for Cutaneous Warts," *Cochrane Database of Systematic Reviews*, Issue 9, pp. 1-178, John Wiley & Sons, ed., (2014).
La'Pelusa et al., "An Aberrant Reaction to *Candida albicans* Antigen Used for Recalcitrant Warts Successfully Treated with Oral Prednisone," *JAAD Case Reports*, 4(3):242-244 (2018).
Leiding et al., "Warts and All: Human Papillomavirus in Primary Immunodeficiencies," *The Journal of Allergy and Clinical Immunology*, 130(5):1030-1048 (2012).
Leung, "Treating Common Warts: Options and Evidence," *Aust. Fam. Physician*, 39(12):933-937 (2010).
Levine et al., "Spherule Coccidioidin in Delayed Dermal Sensitivity Reactions of Experimental Animals," *Sabouraudia*, 7(1):20-32 (1969).
Levine et al., "Dermal sensitivity to Coccidioides immitis. A comparison of responses elicited in man by spherulin and coccidioidin," *Am. Rev. Respir. Dis.*, 107(3):379-386 (1973).
Lipke, "An Armamentarium of Wart Treatments," *Clinical Medicine and Research*, 4(4):273-293 (2006).
Majid et al., "Immunotherapy with intralesional *Candida albicans* antigen in resistant or recurrent warts: a study," *Indian J. Dermatol.*, 58(5):360-365 (2013).
Maronn et al., "One-Year Experience with *Candida* Antigen Immunotherapy for Warts and Molluscum," *Pediatric Dermatology*, 25(2):189-192 (2008).
Massing et al., "Natural History of Warts: A Two-Year Study," *Arch. Dermatol.*, 87:306-310 (1963).
Mendoza et al., "Diagnosis, Treatment, and Outcomes of Coccidioidomycosis in Allogeneic Stem Cell Transplantation," *Transpl. Infect. Dis.*, 17(3):380-388 (2015).

(56) References Cited

OTHER PUBLICATIONS

Messersmith, "How to Select and Oversee Contract Research Organizations," *Global Clinical Trials Playbook*, Chapter 5, pp. 39-55 (2012).
Moraes et al., "*Candida albicans* Allergen Immunotherapy in Recurrent Vaginal Candidiasis," *Invest. Allergol. Clin. Immunol.*, 10(5):305-309 (2000).
Moragues et al., "*Candida* Antigens and Immune Responses: Implications for a Vaccine," *Expert Review of Vaccines*, 13:8:1001-1012 (2014).
Muñoz Garza et al., "Intralesional *Candida* Antigen Immunotherapy for the Treatment of Recalcitrant and Multiple Warts in Children," *Pediatric Dermatology*, 32(6):797-801 (2015).
Murphy et al., "Skin testing of guinea pigs and footpad testing of mice with a new antigen for detecting delayed hypersensitivity to *Cryptococcus neoformans*," *Infect. Immun.*, 9(2):404-409 (1974).
Nadeem et al., "Effect of Growth Media, pH and Temperature of Yeast to Hyphal Transition in *Candida albicans*," *Open Journal of Medical Microbiology*, 3:185-192 (2013).
Navalkar et al., "Peptide Based Diagnostics: Are Random-Sequence Peptides More Useful than Tiling Proteome Sequences?" *Journal of Immunological Methods*, 417:10-21 (2015).
Newman et al., "Clinical Pearls in Dermatology 2017," *Disease-A-Month* 63(7):165-175 (2017).
Nofal et al., "Intralesional Antigen Immunotherapy for the Treatment of Warts: Current Concepts and Future Prospects," *Am. J. Clin. Dermatol.*, 14:253-260 (2013).
Nofal et al., "Significance of Interferon Gamma in the Prediction of Successful Therapy of Common Warts by Intralesional Injection of *Candida* Antigen," *Intl J. Dermatology*, 56:1003-1009 (2017).
Nofal et al., "Combined Acitretin and *Candida* Antigen Versus Either Agent Alone in the Treatment of Recalcitrant Warts," *J. Am. Acad. Dermatol.*, 79(2):377-378 (2018).
Ohri et al., "Pediatric Case Series Evaluating a Standardized *Candida albicans* Skin Test Product," *The Annals of Pharmacotherapy*, 38:973-977 (2004).
Oswald et al., "Wart (Verruca) Treatment," *Pfenninger & Fowler's Procedures for Primary Care*, 3d ed., Section 2—Dermatology, Chap. 42, pp. 267-274, Pfenninger et al. (eds.), Elsevier, Philadelphia, PA (2011).
Pappagianis et al., "Evaluation of the Protective Efficacy of the Killed *Coccidioides immitis* Spherule Vaccine in Humans," *Am. Ref. Respir. Dis.*, 148(3):656-660 (1993).
Pappagianis et al., "Revision and Return of a Coccidioidal Skin Test Reagent," *Mycopathologia*, 174:351-352 (2012).
Perman et al., "The Painful Purple Digit: An Alarming Complication of *Candida albicans* Antigen Treatment of Recalcitrant Warts," *Dermatitis: Contact, Atopic, Occupational, Drug*, 16(1):38-40 (2005).
Phillips et al., "Treatment of Warts with *Candida* Antigen Injection," *Arch. Dermatol.*, 136(10):1274-1275 (2001).
Reiss et al., "Serological and cellular immune activity of peptidoglucomannan fractions of *Candida albicans* cell walls," *Infect. Immun.*, 9(5):881-890 (1974).
Richman et al., "A procedure for total protein determination with special application to allergenic extract standardization," *Journal of Biological Standardization*, 16:225-238 (1988).
Rose et al., "Interpretation of the Tuberculin Skin Test," *J. Gen. Intern. Med.*, 10:635-642 (1995).
Rosenberg, "Immunotherapy of Alopecia Areata with Intralesional *Candida* Antigen," *Pediatr. Dermatol.*, 23(3):299 (2006).
Ruiz-Herrera et al., "Molecular organization of the cell wall of *Candida albicans* and its relation to pathogenicity," *FEMS Yeast Res.*, 6(1):14-29 (2006).
Sadeghi-Gariz et al., "Evaluation of Relative Potency of Human Tuberculin Skin Test in the Guinea Pigs Sensitized with *Mycobacterium Tuberculosis*, *M. bovix* BCG and *M. avium*," *Zahedan J. Res. Med. Sci.*, 15(12):1-4 (2013).
Salt et al., "Risk Factors for Targeted Fungal and Mycobacterial Infections in Patients Taking TNF-alpha Inhibitors," *Arthritis & Rheumatology*, 68(3):1-25 (2015).
Savolainen et al. "In-house reference (IHR) preparation of *Candida albicans* allergen extract A standardized extraction procedure," *Allergy* 53:359-366 (1998).
Savolainen et al. "Allergenic Variability of Different Strains of *Candida albicans*," *Int Arch Allergy Immunol* 90:61-66 (1989).
Seyedmousavi et al., "Isavuconazole, a Broad-Spectrum Triazole for the Treatment of Systemic Fungal Diseases," *Expert Rev. Anti. Infect. Ther.*, 13(1):9-27 (2015).
Signore, "*Candida* Immunotherapy of Warts," *Arch. Dermatol*, 137:1250-1251 (2001).
Signore et al., "*Candida albicans*, Intralesional Injection Immunotherapy of Warts," *Cutis*, 70(3):185-192 (2002).
Slater et al., "Comparison of Total Protein Profile of Alternaria Alternata Extract Obtained from Various U.S. Allergenic Extract Manufacturers," *J. Allergy Clin. Immunol.*, 133(2 Suppl.):AB100, Abstract 346 (2014).
Sloan et al., "Carbon Dioxide Laser-Treatment of Resistance Verrucae Vulgaris: Retrospective Analysis," *Journal of Cutaneous Medicine and Surgery*, 2(3):142-145 (1998).
Smith et al., "Epidemiology of Acute Coccidioidomycosis with Erythema Nodosum," *Am. J. Public Health Nations Health*, 30(6):600-611 (1940).
Smith et al., "The Use of Coccidioidin," *Am. Rev. Tuberc.*, 54(4):330-360 (1948).
Stevens et al., "Dermal Sensitivity to Different Doses of Spherulin and Coccidioidin," *Chest*, 65(5):530-533 (1974).
Summers et al., "Treatment of recalcitrant verruca vulgaris with *Candida* antigen in patient with human immunodeficiency virus," *J. Drugs Dermatol.*, 8(3):268-269 (2009).
Strockbine et al., "Identification and Molecular Weight Characterization of Antigens from *Candida albicans* that are Recognized by Human Sera," *Infection and Immunity*, 43(2):715-721 (1984).
Surtipanti et al., "Determination of Heavy Metals in Meat, Intestine, Liver, Eggs, and Chicken Using Neutron Activation Analysis and Atomic Absorption Spectrometry," pp. 1-8 (1985).
Thappa et al., "Evolving Role of Immunotherapy in the Treatment of Refractory Warts," *Indian Dermatol. Online J.*, 7(5):364-370 (2016).
Ueno et al., "The mannan of *Candida albicans* lacking β-1,2-linked oligomannosides increases the production of inflammatory cytokines by dendritic cells," *Medical Mycology*, 51:385-395 (2013).
Van Haalen et al., "Warts in primary schoolchildren: prevalence and relation with environmental factors," *BJD British Journal of Dermatology*, 161:148-152 (2009).
Vlahovic et al., "*Candida albicans* Immunotherapy for Verrucae Plantaris," *J. Am. Podiatr. Med. Assoc.*, 105(5):395-400 (2015).
Vogel et al., "Tuberculin Hypersensitivity Associated with Immunization of Guinea Pigs with *Candida albicans* and the Presence of this Organism in Normal Guinea Pigs," Med. Res. and Clin. Laboratories, Veterans Administration Hosp. Atlanta, Georgia, pp. 117-124 (1961).
Walch et al., "Immunization of Mice with Induced Mutants of *Coccidioides immitis*," *Sabouraudia*, 9:173-184 (1971).
Warts refractory to conventional therapy yield to *Candida* antigen. Leawood, Kan: Am Acad Fam Phys*90 Clinical Perspectives.
Wheeler et al., "Risk Stratification with Coccidioidal Skin Test to Prevent Valley Fever Amon Inmates, California, 2015," *J. Correct. Health Care*, 24(4):342-351 (2018).
Wilmer et al., "Goodbye Warts, Hello Vitiligo: *Candida* Antigen-Induced Depigmentation," *Pediatric Dermatology*, 30(6):e214-e215 (2013).
Wong et al., "Intralesional *Candida* antigen for common warts in people with HIV," *J. Cutan. Med. Surg.*, 17(5):313-315 (2013).
Zubritsky et al., "Lymphangitis occurring after intralesional *Candida* antigen for verruca vulgaris," *Dermatol. Online J.*, 22(6):18 (2016).
Khozelmeh et al., "Intralesional Immunotherapy compared to cryotherapy in the treatment of warts," Int J Dermatol 56(4), pp. 474-478 (Jan. 2017) (Hoboken New Jersey, US).
Search report dated Jan. 8, 2024, issued in Chinese Application 201980059582.1.

\* cited by examiner

TREATMENT OF WARTS

CROSS REFERENCE TO RELATED APPLICATIONS

This application is continuation of U.S. patent application Ser. No. 17/378,411, filed Jul. 16, 2021 and now U.S. Pat. No. 11,666,617, which is a division of U.S. patent application Ser. No. 16/532,247, filed Aug. 5, 2019 and now U.S. Pat. No. 11,116,808, which claims the benefit of U.S. Provisional Application No. 62/714,942, filed Aug. 6, 2018 and now expired, and U.S. Provisional Application No. 62/880,742, filed Jul. 31, 2019 and now expired, the contents of each of which are herein incorporated by reference in their entireties.

FIELD OF THE INVENTION

The present disclosure relates to therapeutics having a standardized potency for the complete resolution of common warts and for the prevention of recurrence of common warts.

BACKGROUND OF THE INVENTION

Common warts are infections of the skin caused by human papillomavirus (HPV). The virus initially targets epidermal basal cells and induces hyperplasia and hyperkeratosis, which presents clinically as a wart. While not life threatening, common warts can cause both physical discomfort and embarrassment in patients.

It is estimated that common warts have an overall prevalence of 2 to 20% in the United States. However, current treatment options for common warts vary in their effectiveness and often result in recurrence. Treatments including topical salicylic acid, topical imiquimod, bleomycin injections, cryotherapy, excision, electrocautery, and laser vaporization are employed with various outcomes and side effects.

Immunotherapy using *Candida albicans* antigens has also been studied. However, a range of response levels were reported. See Aldahan A S et al., "Efficacy of intralesional immunotherapy for the treatment of warts: A review of the literature," *Dermatologic Therapy* 2016; 29:197-207, Table 1; and Alikhan A et al., "Use of *Candida* antigen injections for the treatment of verruca vulgaris: A two-year mayo clinic experience," *Journal of Dermatological Treatment* 2016; 27(4): 355-58, 355, Table 2. The inconsistent results may be due to the use of different sources of *Candida* antigen in these studies, having apparently different concentrations and potencies. For example, two studies utilized *Candida* antigens obtained from Hollister-Stier (Alikan et al. at 355 and Perman M et al., "The painful purple digit: an alarming complication of *Candida albicans* antigen treatment of recalcitrant warts," *Dermatitis: Contact, Atopic, Occupational, Drug* 2005; 16(1):38-40, cited in Aldahan et al.), another study utilized *Candida* antigens obtained from Bayer (Johnson et al., "Intralesional injection of mumps or candida skin test antigens: a novel immunotherapy for warts," *Arch Dematol.* 2001; 137:451-55, cited in Aldahan et al. and Alikhan et al.), yet another study utilized *Candida* antigens obtained from Creative Drug Industries (Majid I and Imran S, "Immunotherapy with Intralesional *Candida Albicans* Antigen in Resistant or Recurrent Warts: A Study," *Indian Journal of Dermatology* 2013: 58(5): 360-65, cited in Aldahan et al. and Alikhan et al.), while other studies utilized Candin® manufactured by Allermed Laboratories (Kim K H et al., "Phase 1 clinical trial of intralesional injection of *Candida* antigen for the treatment of warts," *Arch Dematol* 2010, 146(12):1431-33; Pfenninger J L and Fowler G C, "Procedures for Primary Care," Third Edition, Elsevier 2010, 639-43; Signor R J, "*Candida albicans* Intralesional Injection Immunotherapy of Warts," Cutis 2002; 70:185-92, cited in Alikhan et al.; Phillips R C et al., "Treatment of Warts with *Candida* Antigen Injection," *Arch Dematol* 2001, 136(10):1274-5); Wong A and Crawford R I, "Intralesional *Candida* antigen for common warts in people with HIV," *J Cutan Med Surg.* 2013; 17(5): 313-15, cited in Aldahan et al. Some studies also do not report their sources of *Candida* antigens. See Summers P et al., "Treatment of recalcitrant verruca vulgaris with *Candida* antigen in patient with human immunodeficiency virus," *J Drugs Dermatol* 2009; 8(3): 268-69, cited in Aldahan et al.; "Warts Refractory to Conventional Therapy Yield to *Candida* Antigen," *American Academy of Family Practice* 90 *Clinical Perspectives* 1990; Harada S, "Clinical Application of Fungus Extracts and its Culture filtrate in the Treatment of Skin Diseases: (3) *Candida* Vaccine in the Treatment of Warts," *Japanese Journal of Dermatology* 1979; 89(6), 397-402.

In view of the various sources being studied, the dosages reported by volumes and weight by volume (v/w) dilutions therefore do not provide sufficient information to physicians to achieve consistent cure rates of warts. At best, U.S. Pat. No. 6,350,451 to Horn provides dosing of antigens based on initial delayed type hypersensitivity (DTH) responses. See '451 Patent at Example. Therefore, *Candida* antigen compositions having standardized potencies for treatment of warts are desired.

SUMMARY OF THE INVENTION

The present disclosure provides for, and includes, compositions having standardized potencies for use in the treatment of one or more common warts or non-common warts. The present disclosure also provides for, and includes, methods for treating one or more common warts or non-common warts.

In an aspect, the present disclosure provides for, and includes a method for treating a common wart in a subject in need thereof, the method comprises administering one or more intralesional injections to the subject of an amount of a pharmaceutical composition effective for complete resolution of the common wart at a cumulative dose of 2.5 units of potency, where the pharmaceutical composition comprises a filtered extract of *Candida albicans* and secreted antigens.

In an aspect, the present disclosure provides for, and includes a method for treating a common wart in a subject in need thereof, the method comprises administering one or more intralesional injections to the subject of an amount of a pharmaceutical composition capable of complete resolution of the common wart at a cumulative dose of 2.5 units of potency, where the pharmaceutical composition comprises a filtered extract of *Candida albicans* and secreted antigens.

In an aspect, the present disclosure provides for, and includes a method for treating a common wart in a subject in need thereof, the method comprises administering one or more intralesional injections to the subject of an amount of a pharmaceutical composition effective for partial resolution of the common wart at a cumulative dose of 5 units of potency, where the pharmaceutical composition comprises a filtered extract of *Candida albicans* and secreted antigens.

In an aspect, the present disclosure provides for, and includes a method for treating a common wart in a subject in need thereof, the method comprises administering one or more intralesional injections to the subject of an amount of a pharmaceutical composition capable of partial resolution of the common wart at a cumulative dose of 5 units of potency, where the pharmaceutical composition comprises a filtered extract of *Candida albicans* and secreted antigens.

In an aspect, the present disclosure provides for, and includes a method for treating a plurality of common warts in a subject in need thereof, the method comprises administering one or more intralesional injections to the subject of an amount of a pharmaceutical composition effective for partial resolution of the plurality of common warts at a cumulative dose of 5 units of potency, where the pharmaceutical composition comprises a filtered extract of *Candida albicans* and secreted antigens.

In an aspect, the present disclosure provides for, and includes a method for treating a plurality of common warts in a subject in need thereof, the method comprises administering one or more intralesional injections to the subject of an amount of a pharmaceutical composition capable of partial resolution of the plurality of common warts at a cumulative dose of 5 units of potency, where the pharmaceutical composition comprises a filtered extract of *Candida albicans* and secreted antigens.

In an aspect, the present disclosure provides for, and includes a method for treating a plurality of common warts in a subject in need thereof, the method comprises administering one or more intralesional injections to the subject of an amount of a pharmaceutical composition effective for reducing the diameter of each of the plurality of common warts by at least 50% at a cumulative dose of 1 unit of potency, where the pharmaceutical composition comprises a filtered extract of *Candida albicans* and secreted antigens.

In an aspect, the present disclosure provides for, and includes a method for treating a plurality of common warts in a subject in need thereof, the method comprises administering one or more intralesional injections to the subject of an amount of a pharmaceutical composition capable of reducing the diameter of each of the plurality of common warts by at least 50% at a cumulative dose of 1 unit of potency, where the pharmaceutical composition comprises a filtered extract of *Candida albicans* and secreted antigens.

In an aspect, the present disclosure provides for, and includes a method for treating a non-common wart in a subject in need thereof, where the subject has one or more common warts, the method comprises administering one or more intralesional injections to the subject of an amount of a pharmaceutical composition effective for complete resolution of the non-common wart at a cumulative dose of 5 units of potency, where the pharmaceutical composition comprises a filtered extract of *Candida albicans* and secreted antigens.

In an aspect, the present disclosure provides for, and includes a method for treating a non-common wart in a subject in need thereof, where the subject has one or more common warts, the method comprises administering one or more intralesional injections to the subject of an amount of a pharmaceutical composition capable of complete resolution of the non-common wart at a cumulative dose of 5 units of potency, where the pharmaceutical composition comprises a filtered extract of *Candida albicans* and secreted antigens.

In an aspect, the present disclosure provides for, and includes a method for treating a previously treated common wart in a subject in need thereof, the method comprises administering one or more intralesional injections to the subject of an amount of a pharmaceutical composition effective for complete resolution of the previously treated common wart at a cumulative dose of 5 units of potency, where the pharmaceutical composition comprises a filtered extract of *Candida albicans* and secreted antigens.

In an aspect, the present disclosure provides for, and includes a method for treating a previously treated common wart in a subject in need thereof, the method comprises administering one or more intralesional injections to the subject of an amount of a pharmaceutical composition capable of complete resolution of the previously treated common wart at a cumulative dose of 5 units of potency, where the pharmaceutical composition comprises a filtered extract of *Candida albicans* and secreted antigens.

In an aspect, the present disclosure provides for, and includes a method for delaying recurrence of a common wart in a subject in need thereof, the method comprises administering one or more intralesional injections to the subject of an amount of a pharmaceutical composition effective for delaying the reappearance of the common wart upon resolution at a cumulative dose of 2.5 units of potency, where the pharmaceutical composition comprises a filtered extract of *Candida albicans* and secreted antigens.

In an aspect, the present disclosure provides for, and includes a method for delaying recurrence of a common wart in a subject in need thereof, the method comprises administering one or more intralesional injections to the subject of an amount of a pharmaceutical composition capable of delaying the reappearance of the common wart upon resolution at a cumulative dose of 2.5 units of potency, where the pharmaceutical composition comprises a filtered extract of *Candida albicans* and secreted antigens.

In an aspect, the present disclosure provides for, and includes a medicament comprising a filtered extract of *Candida albicans* and secreted antigens formulated for complete resolution of a common wart at a cumulative dose of 2.5 units of potency.

In an aspect, the present disclosure provides for, and includes a medicament comprising a filtered extract of *Candida albicans* and secreted antigens formulated for partial resolution of a common wart at a cumulative dose of 5 units of potency.

In an aspect, the present disclosure provides for, and includes a medicament comprising a filtered extract of *Candida albicans* and secreted antigens formulated for reducing the diameter of a common wart by at least 50% at a cumulative dose of 1 unit of potency.

In an aspect, the present disclosure provides for, and includes a medicament comprising a filtered extract of *Candida albicans* and secreted antigens formulated for partial resolution of a plurality of common warts at a cumulative dose of 5 units of potency.

In an aspect, the present disclosure provides for, and includes a medicament comprising a filtered extract of *Candida albicans* and secreted antigens formulated for reducing the diameter of a plurality of common warts by at least 50% at a cumulative dose of 1 unit of potency.

In an aspect, the present disclosure provides for, and includes a medicament comprising a filtered extract of *Candida albicans* and secreted antigens formulated for complete resolution of a non-common wart at a cumulative dose of 5 units of potency.

In an aspect, the present disclosure provides for, and includes a medicament comprising a filtered extract of *Candida albicans* and secreted antigens formulated for complete resolution of a previously treated common wart at a cumulative dose of 5 units of potency.

In an aspect, the present disclosure provides for, and includes a medicament comprising a filtered extract of

*Candida albicans* and secreted antigens formulated for delaying the reappearance of the common wart upon resolution at a cumulative dose of 2.5 units of potency.

In an aspect, the present disclosure provides for, and includes, a method for reducing the level of IL-23 in a subject in need thereof, the method comprises administering one or more intralesional injections to the subject of an amount of a pharmaceutical composition at a cumulative dose of 1 unit of potency, where the pharmaceutical composition comprises a filtered extract of *Candida albicans* and secreted antigens. In an aspect, a subject is diagnosed with at least one common wart. In one aspect, a method of the present disclosure reduces the level of IL-23 for at least about 15% in a subject upon receipt of a cumulative dose of a pharmaceutical composition of the present disclosure when compared to a level of IL-23 measured in the subject before the administering step. In an aspect, a method of the present disclosure reduces the level of IL-23 for at least about 35% in a subject upon receipt of a cumulative dose of a pharmaceutical composition of the present disclosure when compared to a level of IL-23 measured in the subject before the administering step.

In an aspect, the present disclosure provides for, and includes, a method for completely resolving a common wart in a subject in need thereof, the method comprises reducing the level of IL-23 by at least about 15% in a subject in need thereof. In an aspect, the present disclosure provides for, and includes, a method for completely resolving a common wart in a subject in need thereof, the method comprises reducing the level of IL-23 by at least about 35% in a subject in need thereof. In one aspect, a method of the present disclosure reduces the level of IL-23 by administering one or more intralesional injections to the subject of an amount of a pharmaceutical composition at a cumulative dose of 3 units of potency, where the pharmaceutical composition comprises a filtered extract of *Candida albicans* and secreted antigens.

In an aspect, the present disclosure provides for, and includes, a method for reducing the level of IL-7 in a subject in need thereof, the method comprises administering one or more intralesional injections to the subject of an amount of a pharmaceutical composition at a cumulative dose of 0.6 units of potency, where the pharmaceutical composition comprises a filtered extract of *Candida albicans* and secreted antigens. In an aspect, a subject is diagnosed with at least one common wart. In one aspect, a method of the present disclosure reduces the level of IL-7 for at least about 10% in a subject upon receipt of a cumulative dose of a pharmaceutical composition of the present disclosure when compared to a level of IL-7 measured in the subject before the administering step.

In an aspect, the present disclosure provides for, and includes, a method for reducing the level of IL-7 in a subject in need thereof, the method comprises administering one or more intralesional injections to the subject of an amount of a pharmaceutical composition at a cumulative dose of 3 units of potency, where the pharmaceutical composition comprises a filtered extract of *Candida albicans* and secreted antigens. In an aspect, a subject is diagnosed with at least one common wart. In one aspect, a method of the present disclosure reduces the level of IL-7 for at least about 20% in the subject upon receipt of a cumulative dose of a pharmaceutical composition of the present disclosure when compared to a level of IL-7 measured in the subject before the administering step.

In an aspect, the present disclosure provides for, and includes, a method for reducing the level of IP-10 in a subject in need thereof, the method comprises administering one or more intralesional injections to the subject of an amount of a pharmaceutical composition at a cumulative dose of 3 units of potency, where the pharmaceutical composition comprises a filtered extract of *Candida albicans* and secreted antigens. In an aspect, a subject is diagnosed with at least one common wart. In one aspect, a method of the present disclosure reduces the level of IP-10 for at least about 5% in the subject upon receipt of a cumulative dose of a pharmaceutical composition of the present disclosure when compared to a level of IP-10 measured in the subject before the administering step.

In an aspect, the present disclosure provides for, and includes a medicament comprising a filtered extract of *Candida albicans* and secreted antigens used for reducing the level of IL-23 in a subject in need thereof. In an aspect, a subject is diagnosed with at least one common wart.

In an aspect, the present disclosure provides for, and includes a medicament comprising a filtered extract of *Candida albicans* and secreted antigens used for completely resolving a common wart in a subject in need thereof by reducing the level of IL-23 by at least about 35% in a subject in need thereof. In an aspect, the present disclosure provides for, and includes a medicament comprising a filtered extract of *Candida albicans* and secreted antigens used for completely resolving a common wart in a subject in need thereof by reducing the level of IL-23 by at least about 15% in a subject in need thereof.

In an aspect, the present disclosure provides for, and includes a medicament comprising a filtered extract of *Candida albicans* and secreted antigens used for reducing the level of IL-7 in a subject in need thereof. In an aspect, a subject is diagnosed with at least one common wart.

In an aspect, the present disclosure provides for, and includes a medicament comprising a filtered extract of *Candida albicans* and secreted antigens used for reducing the level of IP-10 in a subject in need thereof. In an aspect, a subject is diagnosed with at least one common wart.

BRIEF DESCRIPTION OF THE DRAWINGS

The present disclosure is disclosed with reference to the accompanying drawings, where.

DETAILED DESCRIPTION

Figure 1:
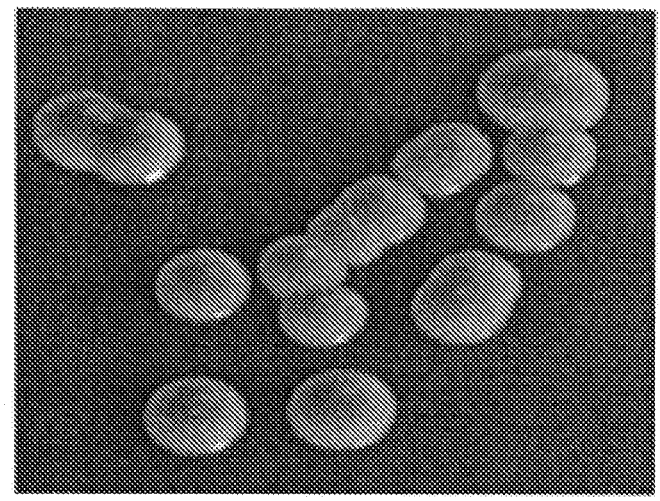
FIG. 1 shows characteristic morphology of isolated colonies of a first strain of *Candida albicans*, deposited as ATCC Accession No. PTA-126019, in accordance with the present disclosure.

The present disclosure provides for, and includes, pharmaceutical compositions having standardized potencies for use in the treatment of one or more common warts or non-common warts. In one aspect, treatment of one or more common warts or non-common warts refers to therapeutic treatment of these warts. In an aspect, treatment of one or more common warts or non-common warts refers to providing prophylactic or preventative measures against the development of warts. In an aspect, a pharmaceutical composition of the present disclosure is capable of complete resolution of one or more common warts and non-common warts with a cumulative dose given in units of potency in accordance with the present disclosure. In one aspect, a pharmaceutical composition of the present disclosure is capable of partial resolution of one or more common warts with a cumulative dose given in units of potency in accordance with the present disclosure. In an aspect, a pharmaceutical composition of the present disclosure is capable of delaying the reappearance of one or more common warts upon resolution with a cumulative dose given in units of potency in accordance with the present disclosure.

The present disclosure also provides for, and includes, methods for treating one or more common warts or non-common warts using the pharmaceutical compositions described herein. In an aspect, methods for completely resolving one or more common warts or non-common warts are provided. In one aspect, methods for partially resolving one or more common warts are provided. In an aspect, methods for treating previously treated common warts are provided. In one aspect, methods for delaying reappearance of common warts are provided.

Unless defined otherwise herein, terms are to be understood according to conventional usage by those of ordinary skill in the relevant art. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York).

All publications, patents, and patent applications mentioned in this disclosure are herein incorporated by reference to the same extent as if each individual publication, patent, or patent application was specifically and individually indicated to be incorporated by reference.

The term "and/or" when used in a list of two or more items, means that any one of the listed items can be employed by itself or in combination with any one or more of the listed items. For example, the expression "A and/or B" is intended to mean either or both of A and B, i.e., A alone, B alone, or A and B in combination. The expression "A, B and/or C" is intended to mean A alone, B alone, C alone, A and B in combination, A and C in combination, B and C in combination, or A, B, and C in combination.

As used herein, terms in the singular and the singular forms "a," "an," and "the," for example, include plural referents unless the content clearly dictates otherwise.

Where a range of values is provided, it is understood that each intervening value, between the upper and lower limit of that range and any other stated or intervening value in that stated range is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either both of those included limits are also included in the disclosure. Whenever the phrase "comprising" is used, variations such as "consisting essentially of" and "consisting of" are also contemplated.

The term "about," as used herein, is intended to qualify the numerical values that it modifies, denoting such a value as variable within a margin of error. When no particular margin of error, such as a standard deviation to a mean value, is recited, the term "about" should be understood to mean that range which would encompass the recited value and the range which would be included by rounding up or down to that figure, taking into account significant figures.

As used herein, a "pharmaceutical composition" of the present disclosure can be an antigen or solvates thereof, described herein.

As used herein, an "excipient" refers to a substance formulated alongside the active ingredient of a medication. An excipient can be used for the purpose of long-term stabilization or to confer a therapeutic enhancement on the active ingredient in the final dosage form, such as facilitating active ingredient absorption, reducing viscosity, or enhancing solubility. Excipients can also be useful in the manufacturing process, to aid in the handling of the active substance concerned such as by facilitating powder flowability or non-stick properties, in addition to aiding in vitro stability such as prevention of denaturation or aggregation over the expected shelf life.

As used herein, "pharmaceutically acceptable carrier" includes any and all solvents, dispersion media, antibacterial and antifungal agents, isotonic and absorption delaying agents and the like. The use of such media and agents for pharmaceutically active substances is well known in the art. Except insofar as any conventional media or agent is incompatible with the pharmaceutical compositions, its use in pharmaceutical compositions is contemplated. As used herein, the phrase "pharmaceutically, pharmacologically, or physiologically acceptable" refers to molecular entities and compositions that do not produce adverse, allergic, or other untoward reactions when administered to an animal or a human. A pharmaceutically acceptable carrier can be liquid (e.g., saline), gel or solid form of diluents, adjuvant, excipients or an acid resistant encapsulated ingredient. Suitable diluents and excipients include pharmaceutical grades of physiological saline, dextrose, glycerol, mannitol, lactose, starch, magnesium stearate, sodium saccharin, cellulose, magnesium carbonate, and the like, and combinations thereof.

As used herein, the term "pharmaceutically acceptable solvate" refers to an association of one or more solvent molecules and a compound of the present disclosure. Examples of solvents that form pharmaceutically acceptable solvates include, but are not limited to, water, isopropanol, ethanol, methanol, DMSO, ethyl acetate, acetic acid, and ethanolamine.

As used herein, the term "treating" refers to (i) completely or partially inhibiting a disease, disorder or condition, for example, arresting its development; (ii) completely or partially relieving a disease, disorder or condition, for example, causing regression of the disease, disorder and/or condition; or (iii) completely or partially preventing a disease, disorder or condition from occurring in a patient that may be predisposed to the disease, disorder and/or condition, but has not yet been diagnosed as having it. Similarly, "treatment" refers to both therapeutic treatment and prophylactic or preventative measures. For example, a method or composition provided here can be used to delay the progression of a condition (e.g., warts). As used herein, "delaying" the progression of a condition means to defer, hinder, slow, retard, stabilize, and/or postpone development of the condition. This delay can be of varying lengths of time, depending on the history of the condition and/or individual being treated.

As used herein, the term "wart" refers to a growth on the skin caused by human papillomavirus.

As used herein, the term "anatomical region" refers to any one of the following regions of a subject's body: left arm, right arm, left hand, right hand, left leg, right leg, left foot, right foot, and torso. As used herein, an arm region includes a shoulder, upper and lower arms, a wrist, and half of an armpit. As used herein, a hand region starts from the distal to the wrist, excluding any periungual warts. As used herein, a foot starts from the distal to ankles, excluding the sole of the foot. As used herein, a leg region includes the upper leg, the lower leg, and an ankle. As used herein, a torso region includes the neck, the back, the chest, the abdomen, the hips, the buttocks and the pelvic region.

As used herein, the term "recalcitrant wart" refers to a wart that was not successfully treated by prior treatment, excluding over-the-counter treatments. As used herein, the term "over-the-counter treatment" refers to medications sold directly to a consumer without a prescription from a healthcare professional.

As used herein, the term "perimeter" refers to the peripheral margin of a wart.

As used herein, the term "recurrence" refers to the growth of a wart at the same location where a previously regressed wart was present.

As used herein, the term "complete resolution" refers to a sustained resolution of a wart reflected by a lack of recurrence of a wart as observed at least 20 weeks from administration of the first intralesional injection.

As used herein, the term "partial resolution" refers to any reduction in the diameter of a wart as compared to the diameter observed before the first intralesional injection.

As used herein, the terms "administer," "administering," or "administration" in reference to a dosage form of the disclosure refers to the act of introducing the dosage form into the system of subject in need of treatment. When a dosage form of the disclosure is given in combination with one or more other active agents (in their respective dosage forms), "administration" and its variants are each understood to include concurrent and/or sequential introduction of the dosage form and the other active agents. Administration of any of the described dosage forms includes simultaneous (parallel) administration, sequential (stepwise) administration, co-administration, or separate administration, in which the therapies are administered separately at approximately the same time, e.g., within about a few seconds to a few hours of one another.

As used herein, the term "medicament" refers to a substance used to treat an illness.

As used herein, the term "molecular weight" refers to the average mass of a molecule of interest to one-twelfth of the mass of carbon 12. A molecular weight is given in the unit of Daltons (Da). A molecular weight is measured by a method using a superpose 12 column calibrated with dextran standards having molecular weights between 1 kilodalton and 512 kilodalton.

As used herein, the term "IL-23" refers to interleukin 23, which is a heterodimeric cytokine having a p19 and p 40 subunit.

As used herein, the term "IL-7" refers to interleukin 7, which is a cytokine important for B and T cell development.

As used herein, the term "IP-10" refers to interferon gamma-induced protein, which is also known as CXCL10.

A. Manufacturing Process of Pharmaceutical Compositions

In one aspect, a pharmaceutical composition of the present disclosure comprising a filtered extract of *Candida albicans* and secreted antigens can be prepared by a series of steps comprising growing two or more strains of *Candida albicans* separately, pooling cultures of two or more strains of *Candida albicans* and dialyzing the mixture, heating the mixture, lyophilizing the heated dialyzed material, producing a dry powder, extracting the dry powder, filtering the extract, and producing a master lot filtered solution. In an aspect, a pharmaceutical composition of the present disclosure can be produced by the protocol as outlined in Example 1.

In an aspect, a pharmaceutical composition of the present disclosure may be prepared using two or more strains of *Candida albicans*, such as using two strains, three strains, four strains, five strains, six strains, seven strains, eight strains, nine strains, or ten strains. In one aspect, a pharmaceutical composition of the present disclosure is prepared using two strains of *Candida albicans*. In an aspect, a pharmaceutical composition of the present disclosure is prepared using strains of *Candida albicans* provided in Hasenclever H F and Mitchell W O, "Antigenic Studies of *Candida*," *Journal of Bacteriology* 1961; 82:578-581. In an aspect, a pharmaceutical composition of the present disclosure is prepared using two strains of *Candida albicans*, where a representative sample of a first strain has been deposited with the ATCC under ATCC Accession No. PTA-126019, and a representative sample of a second strain has been deposited with the ATCC under ATCC Accession No. PTA-126020. In an aspect, a representative sample of a first strain has been deposited with the ATCC under ATCC Accession No. ATCC-10231.

In one aspect, a master lot filtered solution can be diluted at about 2:998 by volume with a diluent to form a pharmaceutical composition, meaning that 2 ml of a master lot filtered solution is diluted with 988 ml of a diluent. In an aspect, a master lot filtered solution can be diluted at a range of from about 2:998 to about 1:1 by volume with a diluent, such as from about 2:998 to about 10:990, from about 10:990 to about 20:980, from about 20:980 to about 30:970, from about 30:970 to about 40:960, from about 40:960 to about 50:950, from about 50:950 to about 60:940, from about 60:940 to about 70:930, from about 70:930 to about 80:920, from about 80:920 to about 90:910, from about 90:910 to about 1:9, from about 1:9 to about 1:8, from about 1:8 to about 1:7, from about 1:7 to about 1:6, from about 1:6 to about 1:5, from about 1:5 to about 1:4, from about 1:4 to about 1:3, from about 1:3 to about 1:2, from about 1:2 to about 1:1. In an aspect, a master lot filtered solution is undiluted in a pharmaceutical composition.

In an aspect, the present disclosure provides for a resulting pharmaceutical composition comprising at least 80% mannose, such as from 80% mannose to 85% mannose, from 85% mannose to 90% or mannose from 80% to 90% mannose. In an aspect, the present disclosure provides for a resulting pharmaceutical composition comprising at least 8% glucose, such as from 8% glucose to 10% glucose, from 10% glucose to 12% glucose, or from 8% glucose to 12% glucose. In an aspect, the present disclosure provides for a resulting pharmaceutical composition comprising at least 1% galactose, such as from 1% galactose to 2.5% galactose, from 2.5% galactose to 5% galactose, or from 1% to 5% galactose.

In an aspect, the present disclosure provides for a resulting pharmaceutical composition comprising antigens having a molecular weight of about 167 kilodaltons, such as from 157 kilodaltons to 177 kilodaltons. In an aspect, a molecular weight is measured by a method using a superpose 12 column calibrated with dextran standards having molecular weights between 1 kilodalton and 512 kilodalton.

B. Test for Relative Potency

A unit of potency in accordance with the present disclosure is defined by a relative potency (RP) compared to a reference standard *Candida albicans* extract. A compound determined to have a relative potency of 1 compared to the standard is assigned to have a potency of 1 unit per mL. Relative potency is determined in a female IAF Hairless guinea pig (Crl:HA-HO) model, compared to a standard *Candida albicans* extract that is capable of eliciting an induration response ≥5 mm in an immunologically competent person at 48 hours after a 0.1 mL injection. In an aspect, a reference standard is established by skin test titration in humans with delayed-type hypersensitivity to *Candida albicans*.

Female IAF Hairless guinea pigs are selected to be as uniform in age and weight as possible. In an aspect, twenty or less female IAF Hairless guinea pigs can be used in a study. They are generally 4-6 months of age, and their body weights at treatment commencement will range from approximately 0.6-0.8 kilograms. All study animals are acclimatized to their designated housing at least 14 days prior to the first day of use.

At week 0, all study animals are sensitized with a 1:1 mixture of Complete Freund's Adjuvant (CFA) mixed with an antigen solution. In an aspect, an antigen solution is a 10-fold dilution of the standard *Candida albicans* extract using unpreserved saline. In another aspect, an antigen solution can be a 100-fold dilution of the standard *Candida albicans* extract using unpreserved saline. In an aspect, Adjulite CFA (Pacific Immunology) or any other commercially available CFA can be used in this assay. Animals are injected using a needle with a maximum of 4 subcutaneous injections of 0.1 ml, or 0.4 ml total, of the prepared mixture. In an aspect, a needle can be a 21 g needle, a 22 g needle, or a 23 g needle. These injections may be given in the cervical region (either the nape or over the shoulders), the gluteal (maximum of two injections in each location, one on each side), and/or the inguinal areas (a maximum of 0.1 ml may be given in each inguinal area). Any one injection regimen containing CFA can be applied to each guinea pig in the study.

Figure 5:
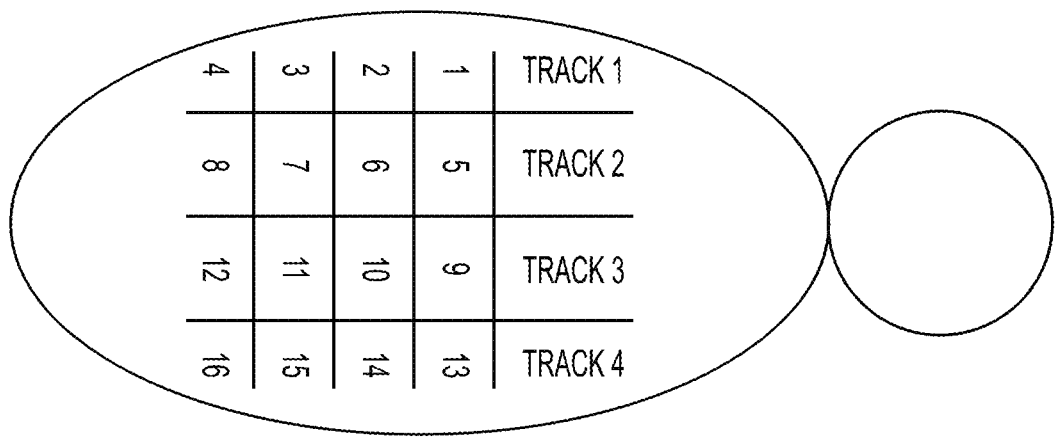
FIG. 5 illustrates an example of a track grid on the back of a guinea pig in accordance with the present disclosure.

At week 4±1 week, four serial dilutions of each test sample and the standard are prepared independently with phenolated normal saline. For example, a set of serial dilutions can be prepared at 1:1, 1:4, 1:16, and 1:64. Animals are sedated for intradermal injection to ensure proper placement. Injections are given at a volume of 0.1 mL using a 27 g intradermal bevel needle on the backs of the sensitized guinea pigs. Injection locations are separated by at least 3 cm apart on a grid on the back of the guinea pigs. For example, four "tracks" can be outlined on the back of a guinea pig to for injections of a standard (Track 1) and three test samples (Tracks 2-4). Each of the "tracks" can be arranged such that the dilutions increase from the last diluted (positioned cranially), to the most diluted (positioned caudally), with all "tracks" being parallel to the spine. See FIG. 5 for an illustration of an example of a track grid on the back of a guinea pig.

At 24 hours±4 hours following injections, animals are restrained by hand, and indurations are marked and measured using a modified Mantoux procedure: With a ruler, the longest possible diameter (in mm) and its midpoint orthogonal diameter (in mm) of the indurated area are recorded. The reaction (response) at each test site is determined by averaging the longest and orthogonal axis measurements. Alternatively, a calibrated caliper may be used. Optionally, the above measurements can be repeated at 48 hours±4 hours.

$Log(RP2)=(\alpha_2\alpha_1)/\beta$ In an aspect, for each guinea pig, responses of Tracks 2, 3 and 4 vs Track 1 are plotted against their corresponding dilution and analyzed using the parallel line method: First, Track 2 and Track 1 response data against log(dilution) are plotted on the same graph, and the linearity of the responses in each track's data is tested, followed by the test for parallelism of the two lines. If the two lines are parallel, then RP2 is calculated using the equation $Log(RP2)=(\alpha_2-\alpha_1)/\beta$, where $\alpha_2$ is the Y-intercept of Track 2, $a_1$ is the Y-intercept of Track 1, and $\beta$ is the common slope of the plotted lines. The same calculation is repeated for Tracks 3 and 4 vs Track 1 to obtain RP3 and RP4, respectively, using the same equation above with $\alpha_2$ replaced with either $\alpha_3$ or $\alpha_4$.

In an aspect, for each guinea pig, responses of Tracks 2, 3 and 4 vs Track 1 are plotted against their corresponding dilution and analyzed using the slope-ratio method: First, Track 2 and Track 1 response data against dilution are plotted on the same graph, the linearity of the responses in each track's data is tested with the regression model $E(Y)=\alpha+\beta D$, where $\alpha$ denotes a common intercept Y-intercept shared by the two plots, $\beta_t$ denotes the slope of the test line (e.g. Track 2), and $\beta_r$ denotes the slope of the reference line (e.g. Track 1). Two validity criteria must be met before using the slop-ratio method of analysis: (1) the slopes of the two tracks are significantly different from zero at $\alpha$-level of 0.05; and (2) the intercept of the test line and that of the reference line are statistically equal, which means that the 90% confidence interval for the difference in the intercepts contains 0. If the above criteria are met, an estimate of relative potency, RP2, is calculated as RP2=estimate of $(\beta_t)$/estimate of $(\beta_r)$. The same calculation is repeated for Tracks 3 and 4 vs Track 1 to obtain RP3 and RP4, respectively, using the same equation above with $\alpha_2$ replaced with either $\alpha_3$ or $\alpha_4$.

After RP2, RP3, and RP4 are obtained, these are plotted against the RP of Track 1. A regression analysis is performed to obtain the coefficient of determination denoted by $R^2$. The $R^2$ is targeted to be ≥0.85. Each of RP2, RP3, and RP4 are the relative potencies of the respective sample in that track.

A relative potency of 1 denotes that a test sample has the same potency as the reference standard.

C. Formulation

One or more components of a pharmaceutical composition of the present disclosure can be formulated in admixture with conventional excipients, carriers, buffers, etc. In an aspect, an excipient is a substance formulated alongside the active ingredient of a medication. Typical carriers include, but are not limited to: water; salt solutions; alcohols; gum arabic; vegetable oils; benzyl alcohols; polyethylene glycols; gelatin; carbohydrates, such as lactose, amylose or starch; magnesium stearate; talc; silicic acid; paraffin; perfume oil; fatty acid esters; hydroxymethylcellulose; polyvinyl pyrrolidone; etc. In an aspect, a carrier includes any and all solvents, dispersion media, antibacterial and antifungal agents, isotonic and absorption delaying agents and the like.

One or more components of a pharmaceutical composition of the present disclosure can be sterilized and, if desired, mixed with auxiliary agents such as: lubricants; preservatives; disintegrants; stabilizers such as cyclodextrans; wetting agents; emulsifiers; salts; buffers; natural or artificial coloring agents; natural or artificial flavoring agents; or aromatic substances.

One or more components of a pharmaceutical composition of the present disclosure can also include one or more of the following agents: acetylated monoglyceride, aspartame, beta carotene, calcium stearate, carnauba wax, cellulose acetate phthalate, citric acid, citric acid anhydrous, colloidal silicon dioxide, confectioner's sugar, crospovidone, docusate sodium, ethyl alcohol, ferric oxide, fructose, gelatin, glycerine, glyceryl monostearate (e.g. glyceryl monostearate 40-50), glyceryl triacetate, HPMC (hydroxypropyl methylcellulose), hydroxypropyl cellulose, hypromellose, iron oxide, isopropyl alcohol, lactose monohydrate, low substituted hydroxypropyl cellulose, magnesium carbonate, magnesium stearate, maltol, mannitol, methacrylic acid, methacrylic acid copolymer (e.g. methacrylic acid copolymer type C), methylcellulose, microcrystalline cellulose, mono ammonium glycyrrhizinate, n-butyl alcohol, paraffin, pectin propylene glycol alginate, polyacrylate, polyethylene glycol (e.g. polyethylene glycol 6000), polysorbate 80, polyvinyl pyrrolidone, povidone, propylene glycol, shellac, silicon dioxide, sodium carbonate, sodium citrate, sodium hydroxide, sodium lauryl sulfate, sodium stearyl fumarate, sorbitol, starch, sucrose, sugar sphere, talc, titanium dioxide, triethyl citrate, and xanthan gum.

In an aspect, a pharmaceutical composition described herein comprises an active compound prepared for administration as solutions of free base or pharmacologically acceptable salts in water suitably mixed with a surfactant, such as hydroxypropylcellulose. Pharmaceutically acceptable base addition salts can be formed with metals or amines, such as alkali and alkaline earth metals or organic amines. Pharmaceutically acceptable salts of compounds can also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N' dibenzylethylenediamine, chloroprocaine, choline, diethanolamine, dicyclohexylamine, ethylenediamine, N methylglucamine, and procaine.

Pharmaceutically acceptable acid addition salts include inorganic or organic acid salts. Examples of suitable acid salts include the hydrochlorides, acetates, citrates, salicylates, nitrates, phosphates. Other suitable pharmaceutically acceptable salts are well known to those skilled in the art and include, for example, acetic, citric, oxalic, tartaric, or mandelic acids, hydrochloric acid, hydrobromic acid, sulfuric acid or phosphoric acid; with organic carboxylic, sulfonic, sulfo or phospho acids or N substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4 aminosalicylic acid, 2 phenoxybenzoic acid, 2 acetoxybenzoic acid, embonic acid, nicotinic acid or isonicotinic acid; and with amino acids, such as the 20 alpha amino acids involved in the synthesis of proteins in nature, for example glutamic acid or aspartic acid, and also with phenylacetic acid, methanesulfonic acid, ethanesulfonic acid, 2 hydroxyethanesulfonic acid, ethane 1,2 disulfonic acid, benzenesulfonic acid, 4 methylbenzenesulfoc acid, naphthalene 2 sulfonic acid, naphthalene 1,5 disulfonic acid, 2 or 3 phosphoglycerate, glucose 6 phosphate, N-cyclohexylsulfamic acid (with the formation of cyclamates), or with other acid organic compounds, such as ascorbic acid.

In an aspect, a pharmaceutical composition of the present disclosure comprises NaCl, $NaHCO_3$, human albumin, polysorbate 80, and phenol. In an aspect, a pharmaceutical composition of the present disclosure comprises 0.5% NaCl, 0.25% $NaHCO_3$, 0.03% human albumin, 8 ppm polysorbate 80, and 0.4% phenol.

In an aspect, a pharmaceutical composition of the present disclosure as described herein can be administered to the subject in need thereof via any route including, but not limited to, sublingual, caudal, dental, endocervical, enteral, epidural, extracorporeal, intravenous, implantation, infiltration, intra-amniotic, intra-arterial, intra-articular, intrabuccal, intra-cardiac, intra-caudal, intra-cavitary, intra-dermal, intra-discal, intralesional, intralymphatic, intraocular, intraperitoneal, intrapleural, intraspinal, intrasynovial, intrathecal, intratracheal, intratumor, intratympanic, intrauterine, intravascular, intravitreal, iontophoresis, irrigation, nasal, parenteral, percutaneous, periarticular, peridural, periodontal, photophoresis, retrobulbar, subarachnoid, subconjunctival, submucosal, transdermal, ureteral, and urethral. In one aspect, a pharmaceutical composition of the present disclosure is administered to the subject in need thereof intralesionally. In one aspect, administering is performed by the act of introducing the dosage form into the system of subject in need of treatment.

In an aspect, a pharmaceutical composition of the present disclosure as described herein can be administered via a form selected from the group consisting of oral, buccal, sublingual, topical, injectable, infused, inhalable, rectal, intravenous, intramuscular, and subcutaneous forms. For example, a pharmaceutical composition of the present disclosure as described herein can be administered as a transdermal patch, in a microneedle, as a mist, as suppository, as a gel, as a cream, as a pill, or as a spray using methods known in the art. In one aspect, a pharmaceutical composition of the present disclosure as described herein is administered via an injectable form.

A pharmaceutical composition provided here can be prepared as pharmaceutical forms suitable for injectable use. In an aspect, such compositions include sterile aqueous solutions or dispersions and sterile powders for the extemporaneous preparation of sterile injectable solutions or dispersions. In all cases the form is sterile and must be fluid to the extent that easy syringability exists. It remains stable under the conditions of manufacture and storage and is preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. In an aspect, a solvent is a pharmaceutically acceptable solvate. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In an aspect, sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In an aspect, a pharmaceutical composition disclosed herein comprises human serum albumin. In one aspect, a pharmaceutical composition disclosed herein comprises polysorbate 80.

In an aspect, a pharmaceutical composition disclosed herein can be formulated as a sterile stabilized filtered extract of *Candida albicans*. In one aspect, a pharmaceutical composition can be formulated in a single dose vial. In an aspect, a pharmaceutical composition can be formulated in a single unpreserved vial. In one aspect, a pharmaceutical composition can be formulated in a multi-dose vial. In an aspect, a pharmaceutical composition can be formulated in a multi-dose preserved vial. In an aspect, a pharmaceutical composition can be formulated as a prefilled syringe or device with or without an attached needle. In an aspect, a pharmaceutical composition can be formulated in a container selected from the group consisting of a needle, a vial, and an ampoule. In an aspect, a container can be a glass container or a plastic container. In one aspect, a container has a volume of about 0.25 ml, about 0.5 ml, about 0.75 ml, about 1.0 ml, about 1.5 ml, about 2.0 ml, about 2.5 ml, about 3.0 ml, about 3.5 ml, about 4.0 ml, about 4.5 ml, about 5 ml, about 6 ml, about 7 ml, about 8 ml, about 9 ml, or about 10 ml.

In an aspect, a medicament comprising a filtered extract of *Candida albicans* and secreted antigens is provided for use in the treatment of warts according to the present disclosure at a cumulative dose provided by the present disclosure. In one aspect, a treatment of warts is selected from the group consisting of complete resolution of a common wart, partial resolution of a common wart, reducing the diameter of a common wart, partial resolution of a plurality of common warts, reducing the diameter of a plurality of common warts by at least 50%, complete resolution of a non-common wart, complete resolution of a previously treated common wart, and delaying the reappearance of the common wart upon resolution. In an aspect, a medicament provides a treatment of warts at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency. In an aspect, a medicament is formulated for administration to a subject by injection. In one aspect, an injection is provided as an intralesional injection.

In an aspect, a medicament comprising a filtered extract of *Candida albicans* and secreted antigens formulated for complete resolution of a common wart at a cumulative dose of 2.5 units of potency is provided. In one aspect, the present disclosure provides for a medicament comprising a filtered extract of *Candida albicans* and secreted antigens formulated for complete resolution of a common wart at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency.

In one aspect, a medicament comprising a filtered extract of *Candida albicans* and secreted antigens formulated for partial resolution of a common wart at a cumulative dose of 5 units of potency is provided. In one aspect, the present disclosure provides for a medicament comprising a filtered extract of *Candida albicans* and secreted antigens formulated for partial resolution of a common wart at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency.

In an aspect, a medicament comprising a filtered extract of *Candida albicans* and secreted antigens formulated for reducing the diameter of a common wart by at least 50% at a cumulative dose of 1 unit of potency is provided. In one aspect, the present disclosure provides for a medicament comprising a filtered extract of *Candida albicans* and secreted antigens formulated for reducing the diameter of a common wart by at least 50% at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency.

In one aspect, a medicament comprising a filtered extract of *Candida albicans* and secreted antigens formulated for partial resolution of a plurality of common warts at a cumulative dose of 5 units of potency is provided. In one aspect, the present disclosure provides for a medicament comprising a filtered extract of *Candida albicans* and secreted antigens formulated for partial resolution of a plurality of common warts at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency.

In an aspect, a medicament comprising a filtered extract of *Candida albicans* and secreted antigens formulated for reducing the diameter of a plurality of common warts by at least 50% at a cumulative dose of 1 unit of potency is provided. In one aspect, the present disclosure provides for a medicament comprising a filtered extract of *Candida albicans* and secreted antigens formulated for reducing the diameter of a plurality of common warts by at least 50% at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency.

In one aspect, a medicament comprising a filtered extract of *Candida albicans* and secreted antigens formulated for complete resolution of a non-common wart at a cumulative dose of 5 units of potency is provided. In one aspect, the present disclosure provides for a medicament comprising a filtered extract of *Candida albicans* and secreted antigens formulated for complete resolution of a non-common wart at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency.

In an aspect, a medicament comprising a filtered extract of *Candida albicans* and secreted antigens formulated for complete resolution of a previously treated common wart at a cumulative dose of 5 units of potency is provided. In one aspect, the present disclosure provides for a medicament comprising a filtered extract of *Candida albicans* and secreted antigens formulated for complete resolution of a previously treated common wart at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency.

In one aspect, a medicament comprising a filtered extract of *Candida albicans* and secreted antigens formulated for delaying the reappearance of the common wart upon resolution at a cumulative dose of 2.5 units of potency is provided. In one aspect, the present disclosure provides for a medicament comprising a filtered extract of *Candida albicans* and secreted antigens formulated for delaying the reappearance of the common wart upon resolution at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency.

In an aspect, a medicament comprising a filtered extract of *Candida albicans* and secreted antigens used for reducing the level of a cytokine biomarker in a subject diagnosed with a common wart is provided. In one aspect, a cytokine biomarker is an inflammatory cytokine. In an aspect, a cytokine biomarker is selected from the group consisting of IL-23, IL-7, and IP-10. In an aspect, the level of a cytokine biomarker in a subject is reduced upon administration of a medicament comprising a filtered extract of *Candida albicans* and secreted antigens at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency. In an aspect, the level of a cytokine biomarker in a subject is reduced upon administration of a medicament comprising a filtered extract of *Candida albicans* and secreted antigens at a cumulative dose of at least about 0.5 unit of potency, at least about 1 unit of potency, at least about 2 units of potency, at least about 3 units of potency, at least about 4 units of potency, at least about 5 units of potency, at least about 6 units of potency, at least about 7 units of potency, at least about 8 units of potency, at least about 9 units of potency, or at least about 10 units of potency. In an aspect, the level of a cytokine biomarker in a subject is reduced upon administration of a medicament comprising a filtered extract of *Candida albicans* and secreted antigens at a cumulative dose from about 0.5 unit of potency to about 10 units of potency, such as from about 0.5 unit of potency to about 9.5 units of potency, from about 1 unit of potency to about 9.5 units of potency, from about 1.5 units of potency to about 9 units of potency, from about 2 units of potency to about 9 units of potency, from about 2 units of potency to about 8.5 units of potency, from about 2.5 units of potency to about 8.5 units of potency, from about 2.5 units of potency to about 8 units of potency, from about 3 units of potency to about 8 units of potency, from about 3 units of potency to about 7.5 units of potency, from about 3.5 units of potency to about 7.5 units of potency, from about 3.5 units of potency to about 7 units of potency, from about 4 units of potency to about 7 units of potency, from about 4 units of potency to about 6.5 units of potency, from about 4.5 units of potency to about 6.5 units of potency, from about 4.5 units of potency to about 6 units of potency, or from about 5 units of potency to about 6 units of potency. In an aspect, the level of a cytokine biomarker level is reduced up to 99.9% in a subject upon administration of a cumulative dose of a medicament, such as up to 99.5%, up to 99%, up to 98%, up to 95%, up to 90%, up to 85%, up to 80%, up to 75%, up to 70%, up to 65%, up to 60%, up to 55%, up to 50%, up to 45%, up to 40%, up to 35%, up to 30%, up to 25%, up to 20%, up to 15%, up to 10%, or up to 5%. In one aspect, the level of a cytokine biomarker level is reduced from about 5% to about 99.9% in a subject upon administration of a cumulative dose of a medicament, such as from about 5% to about 99.8%, from about 5% to about 99.5%, from about 5% to about 99%, from about 5% to about 98%, from about 5% to about 95%, from about 10% to about 95%, from about 10% to about 90%, from about 15% to about 90%, from about 15% to about 85%, from about 20% to about 85%, from about 20% to about 80%, from about 25% to about 80%, from about 25% to about 75%, from about 30% to about 75%, from about 30% to about 70%, from about 35% to about 70%, from about 35% to about 65%, from about 40% to about 65%, from about 40% to about 60%, from about 45% to about 60%, from about 45% to about 55%, or from about 50% to about 55%.

In an aspect, a medicament comprising a filtered extract of *Candida albicans* and secreted antigens used for reducing the level of IL-23 in a subject in need thereof is provided. In an aspect, a subject is diagnosed with at least one common wart.

In an aspect, a medicament comprising a filtered extract of *Candida albicans* and secreted antigens used for completely resolving a common wart in a subject in need thereof by reducing the level of IL-23 by at least about 35% in a subject in need thereof is provided. In an aspect, a medicament comprising a filtered extract of *Candida albicans* and secreted antigens used for completely resolving a common wart in a subject in need thereof by reducing the level of IL-23 by at least about 15% in a subject in need thereof is provided.

In an aspect, a medicament comprising a filtered extract of *Candida albicans* and secreted antigens used for reducing the level of IL-7 in a subject in need thereof is provided. In an aspect, a subject is diagnosed with at least one common wart.

In an aspect, a medicament comprising a filtered extract of *Candida albicans* and secreted antigens used for reducing the level of IP-10 in a subject in need thereof is provided. In an aspect, a subject is diagnosed with at least one common wart.

In an aspect, a medicament for use in the complete resolution of a common wart is provided, where the medicament comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA-126020. In an aspect, a representative sample of a first strain has been deposited with the ATCC under ATCC Accession No. ATCC-10231.

In an aspect, a medicament for use in the partial resolution of a common wart is provided, where the medicament comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA-126020. In an aspect, a representative sample of a first strain has been deposited with the ATCC under ATCC Accession No. ATCC-10231.

In an aspect, a medicament for use in reducing the diameter of a common wart by at least 50% is provided, where the medicament comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA-126020. In an aspect, a representative sample of a first strain has been deposited with the ATCC under ATCC Accession No. ATCC-10231.

In an aspect, a medicament for use in the partial resolution of a plurality of common warts is provided, where the medicament comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA-126020. In an aspect, a representative sample of a first strain has been deposited with the ATCC under ATCC Accession No. ATCC-10231.

In an aspect, a medicament for use in reducing the diameter of a plurality of common warts by at least 50% is provided, where the medicament comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA-126020. In an aspect, a representative sample of a first strain has been deposited with the ATCC under ATCC Accession No. ATCC-10231.

In an aspect, a medicament for use in the complete resolution of a non-common wart is provided, where the medicament comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA-126020. In an aspect, a representative sample of a first strain has been deposited with the ATCC under ATCC Accession No. ATCC-10231.

In an aspect, a medicament for use in the complete resolution of a previously treated common wart is provided, where the medicament comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA-126020. In an aspect, a representative sample of a first strain has been deposited with the ATCC under ATCC Accession No. ATCC-10231.

In an aspect, a medicament for use in delaying the reappearance of the common wart is provided, where the medicament comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA-126020. In an aspect, a representative sample of a first strain has been deposited with the ATCC under ATCC Accession No. ATCC-10231.

In an aspect, a medicament comprising a filtered extract of *Candida albicans* and secreted antigens used for reducing the level of IL-23 in a subject in need thereof is provided, where the medicament comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA-126020. In an aspect, a subject is diagnosed with at least one common wart. In an aspect, a representative sample of a first strain has been deposited with the ATCC under ATCC Accession No. ATCC-10231.

In an aspect, a medicament comprising a filtered extract of *Candida albicans* and secreted antigens used for completely resolving a common wart in a subject in need thereof by reducing the level of IL-23 by at least about 35% in a subject in need thereof is provided, where the medicament comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA-126020. In an aspect, a representative sample of a first strain has been deposited with the ATCC under ATCC Accession No. ATCC-10231.

In an aspect, a medicament comprising a filtered extract of *Candida albicans* and secreted antigens used for reducing the level of IL-7 in a subject in need thereof is provided, where the medicament comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA- 126020. In an aspect, a subject is diagnosed with at least one common wart. In an aspect, a representative sample of a first strain has been deposited with the ATCC under ATCC Accession No. ATCC-10231.

In an aspect, a medicament comprising a filtered extract of *Candida albicans* and secreted antigens used for reducing the level of IP-10 in a subject in need thereof is provided, where the medicament comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA-126020. In an aspect, a subject is diagnosed with at least one common wart. In an aspect, a representative sample of a first strain has been deposited with the ATCC under ATCC Accession No. ATCC-10231.

In an aspect, a medicament comprising a filtered extract of *Candida albicans* and secreted antigens is formulated to have a potency of at least about 1 unit per ml, such as at least about 2 units per ml, at least about 3 units per ml, at least about 4 units per ml, at least about 5 units per ml, at least about 6 units per ml, at least about 7 units per ml, at least about 8 units per ml, at least about 9 units per ml, at least about 10 units per ml, at least about 15 units per ml, at least about 20 units per ml, at least about 25 units per ml, at least about 30 units per ml, at least about 40 units per ml, at least about 50 units per ml, at least about 30 units per ml, at least about units per ml, at least about 50 units per ml, at least about 60 units per ml, at least about 70 units per ml, at least about 80 units per ml, at least about 90 units per ml, or at least about 100 units per ml.

D. Method of Treatment

In an aspect, a method for treating a wart in a subject in need thereof is provided, the method comprises administering one or more doses of a pharmaceutical composition of the present disclosure to a subject in need thereof. In one aspect, a growth on the skin caused by human papillomavirus. In an aspect, a pharmaceutical composition comprises a filtered extract of *Candida albicans* and secreted antigens. In an aspect, a method of the present disclosure completely or partially arrests wart development. In one aspect, a method of the present disclosure completely or partially relieves a wart. In an aspect, a method of the present disclosure causes regression of a wart. In an aspect, a method of the present disclosure completely or partially prevents warts from developing in a patient that may be predisposed to wart development. In one aspect, a treatment of warts is selected from the group consisting of complete resolution of a common wart, partial resolution of a common wart, reducing the diameter of a common wart, partial resolution of a plurality of common warts, reducing the diameter of a plurality of common warts by at least 50%, complete resolution of a non-common wart, complete resolution of a previously treated common wart, and delaying the reappearance of the common wart upon resolution. In an aspect, a method for treating a wart achieves its treatment goal at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency. In an aspect, each dose is administered to a subject by injection. In one aspect, an injection is provided as an intralesional injection.

In an aspect, a method for treating a common wart in a subject in need thereof is provided, the method comprises administering one or more intralesional injections to the subject of an amount of a pharmaceutical composition effective for complete resolution of the common wart at a cumulative dose of 2.5 units of potency, where the pharmaceutical composition comprises a filtered extract of *Candida albicans* and secreted antigens. In one aspect, a method for treating a common wart in a subject in need thereof is provided, the method comprises administering one or more intralesional injections to the subject of an amount of a pharmaceutical composition capable of complete resolution of the common wart at a cumulative dose of 2.5 units of potency, where the pharmaceutical composition comprises a filtered extract of *Candida albicans* and secreted antigens.

In an aspect, complete resolution of a common wart is identified by a lack of recurrence of the common wart at the same site observed at least 20 weeks from administration of the first intralesional injection, such as observed at about 20 weeks, at about 25 weeks, at about 30 weeks, at about 35 weeks, at about 40 weeks, about 45 weeks, about 50 weeks, about 55 weeks, about 60 weeks, about 70 weeks, about 80 weeks, about 90 weeks, or about 100 weeks after administration of the first intralesional injection. In an aspect, recurrence of a common wart is defined by the growth of a wart at the same location where a previously regressed wart was present.

In an aspect, complete resolution of the wart is accompanied by a lack of scarring at the location of the common wart. In one aspect, complete resolution of the wart is accompanied by a low level of hypopigmentation at the location of the common wart, such as less than 3% of all resolved common warts.

In an aspect, a method for treating a common wart in a subject in need thereof is provided, the method comprises administering one or more intralesional injections to the subject of an amount of a pharmaceutical composition effective for partial resolution of the common wart at a cumulative dose of 5 units of potency, where the pharmaceutical composition comprises a filtered extract of *Candida albicans* and secreted antigens. In one aspect, a pharmaceutical composition effective for partial resolution of the common wart at a cumulative dose of 5 units of potency is also effective for reducing the diameter of the common wart by at least 50% at a cumulative dose of 1 unit of potency. In an aspect, partial resolution of a wart is identified by any reduction in the diameter of a wart as compared to the diameter observed before the first intralesional injection.

In an aspect, a method for treating a common wart in a subject in need thereof is provided, the method comprises administering one or more intralesional injections to the subject of an amount of a pharmaceutical composition capable of partial resolution of the common wart at a cumulative dose of 5 units of potency, where the pharmaceutical composition comprises a filtered extract of *Candida albicans* and secreted antigens. In one aspect, a pharmaceutical composition effective for partial resolution of the common wart at a cumulative dose of 5 units of potency is also capable of reducing the diameter of the common wart by at least 50% at a cumulative dose of 1 unit of potency.

In an aspect, a method for treating a plurality of common warts in a subject in need thereof is provided, the method comprises administering one or more intralesional injections to the subject of an amount of a pharmaceutical composition effective for partial resolution of the plurality of common warts at a cumulative dose of 5 units of potency, where the pharmaceutical composition comprises a filtered extract of

*Candida albicans* and secreted antigens. In one aspect, a method for treating a plurality of common warts in a subject in need thereof is provided, the method comprises administering one or more intralesional injections to the subject of an amount of a pharmaceutical composition capable of partial resolution of the plurality of common warts at a cumulative dose of 5 units of potency, where the pharmaceutical composition comprises a filtered extract of *Candida albicans* and secreted antigens.

In an aspect, a method for treating a plurality of common warts in a subject in need thereof is provided, the method comprises administering one or more intralesional injections to the subject of an amount of a pharmaceutical composition effective for reducing the diameter of each of the plurality of common warts by at least 50% at a cumulative dose of 1 unit of potency, where the pharmaceutical composition comprises a filtered extract of *Candida albicans* and secreted antigens. In an aspect, a method for treating a plurality of common warts in a subject in need thereof is provided, the method comprises administering one or more intralesional injections to the subject of an amount of a pharmaceutical composition capable of reducing the diameter of each of the plurality of common warts by at least 50% at a cumulative dose of 1 unit of potency, where the pharmaceutical composition comprises a filtered extract of *Candida albicans* and secreted antigens.

In one aspect, a plurality of common warts comprise 2 to 20 common warts, such as 2 to 20 common warts, 2 to 19 common warts, 3 to 19 common warts, 3 to 18 common warts, 4 to 18 common warts, 4 to 17 common warts, 5 to 17 common warts, 5 to 16 common warts, 6 to 16 common warts, 6 to 15 common warts, 7 to 15 common warts, 7 to 14 common warts, 8 to 14 common warts, 8 to 13 common warts, 9 to 13 common warts, 9 to 12 common warts, 10 to 12 common warts, 10 to 11 common warts, or 11 to 12 common warts. In an aspect, a plurality of common warts are located within the same anatomical location in a subject. In one aspect, a plurality of common warts are located in different anatomical locations in a subject. In an aspect, an anatomical location is selected from one of the following regions of a subject's body: left arm, right arm, left hand, right hand, left leg, right leg, left foot, right foot, and torso. In one aspect, an arm region includes a shoulder, upper and lower arms, a wrist, and half of an armpit. In an aspect, a hand region starts from the distal to the wrist, excluding any periungual warts. In one aspect, a foot starts from the distal to ankles, excluding the sole of the foot. In an aspect, a leg region includes the upper leg, the lower leg, and an ankle. In one aspect, a torso region includes the neck, the back, the chest, the abdomen, the hips, the buttocks and the pelvic region.

In an aspect, a method for treating a non-common wart in a subject in need thereof is provided, where the subject has one or more common warts, and the method comprises administering one or more intralesional injections to the subject of an amount of a pharmaceutical composition effective for complete resolution of the non-common wart at a cumulative dose of 5 units of potency, where the pharmaceutical composition comprises a filtered extract of *Candida albicans* and secreted antigens. In an aspect, a method for treating a non-common wart in a subject in need thereof is provided, where the subject has one or more common warts, and the method comprises administering one or more intralesional injections to the subject of an amount of a pharmaceutical composition capable of complete resolution of the non-common wart at a cumulative dose of 5 units of potency, where the pharmaceutical composition comprises a filtered extract of *Candida albicans* and secreted antigens.

In an aspect, a non-common wart is a plantar wart. In one aspect, a non-common wart is a genital wart. In an aspect, a non-common wart is a facial wart. In one aspect, a non-common wart is a flat wart. In one aspect, a non-common wart is a periungual wart. In an aspect, a non-common wart is located within the same anatomical area as one or more common warts.

In an aspect, complete resolution of a non-common wart is identified by a lack of recurrence of the non-common wart at the same site observed at least 20 weeks from administration of the first intralesional injection, such as observed at about 20 weeks, at about 25 weeks, at about 30 weeks, at about 35 weeks, at about 40 weeks, about 45 weeks, about 50 weeks, about 55 weeks, about 60 weeks, about 70 weeks, about 80 weeks, about 90 weeks, or about 100 weeks after administration of the first intralesional injection. In an aspect, recurrence of a common wart is defined by the growth of a wart at the same location where a previously regressed wart was present.

In one aspect, a method for treating a previously treated common wart in a subject in need thereof is provided, the method comprises administering one or more intralesional injections to the subject of an amount of a pharmaceutical composition effective for complete resolution of the previously treated common wart at a cumulative dose of 5 units of potency, where the pharmaceutical composition comprises a filtered extract of *Candida albicans* and secreted antigens. In an aspect, a method for treating a previously treated common wart in a subject in need thereof is provided, the method comprises administering one or more intralesional injections to the subject of an amount of a pharmaceutical composition capable of complete resolution of the previously treated common wart at a cumulative dose of 5 units of potency, where the pharmaceutical composition comprises a filtered extract of *Candida albicans* and secreted antigens.

In an aspect, a previously treated common wart is a common wart previously treated with cryotherapy. In one aspect, a previously treated common wart did not respond to cryotherapy. In an aspect, a cryotherapy did not completely resolve a previously treated common wart.

In one aspect, a previously treated common wart is a common wart previously treated with salicylic acid or a related acid. In an aspect, a related acid is trichloroacetic acid or bichloroacetic acid. In an aspect, a previously treated common wart did not respond to salicylic acid or a related acid. In one aspect, salicylic acid or a related acid did not completely resolve a previously treated common wart.

In an aspect, a previously treated common wart is a common wart previously treated with a treatment selected from the group consisting of liquid nitrogen, carbon dioxide, cantharidin, simple occlusion, wart gel, apple cider vinegar, surgery, laser, tea tree oil, freeze wart spray, wart scraped, electrodessication, essential oils of lavender and oregano, and imiquimod. In one aspect, a previously treated common wart did not respond to a prior treatment. In an aspect, a prior treatment did not completely resolve a previously treated common wart.

In an aspect, complete resolution of a previously treated common wart is identified by a lack of recurrence of the previously treated common wart at the same site observed at least 20 weeks from administration of the first intralesional injection, such as observed at about 20 weeks, at about 25 weeks, at about 30 weeks, at about 35 weeks, at about 40 weeks, about 45 weeks, about 50 weeks, about 55 weeks, about 60 weeks, about 70 weeks, about 80 weeks, about 90 weeks, or about 100 weeks after administration of the first intralesional injection. In an aspect, recurrence of a common wart is defined by the growth of a wart at the same location where a previously regressed wart was present.

In an aspect, complete resolution of the previously treated common wart is accompanied by a lack of scarring at the location of the common wart. In one aspect, complete resolution of the previously treated common wart is accompanied by a low level of hypopigmentation at the location of the common wart, such as less than 3% of all resolved common warts.

In one aspect, a method for delaying recurrence of a common wart in a subject in need thereof is provided, the method comprises administering one or more intralesional injections to the subject of an amount of a pharmaceutical composition effective for delaying the reappearance of the common wart upon resolution at a cumulative dose of 2.5 units of potency, where the pharmaceutical composition comprises a filtered extract of *Candida albicans* and secreted antigens. In one aspect, a method for delaying recurrence of a common wart in a subject in need thereof is provided, the method comprises administering one or more intralesional injections to the subject of an amount of a pharmaceutical composition capable of delaying the reappearance of the common wart upon resolution at a cumulative dose of 2.5 units of potency, where the pharmaceutical composition comprises a filtered extract of *Candida albicans* and secreted antigens. In an aspect, delaying the recurrence of a common wart means to defer, hinder, slow, retard, stabilize, and/or postpone development of the condition at the same location where a previously regressed wart was present. In one aspect, the delay can be of varying lengths of time, depending on the history of the condition and/or individual being treated. In an aspect, a subject does not develop any new common warts within at least 16 weeks after the last injection of the treatment regimen, such as at least 18 weeks, at least 20 weeks, at least 25 weeks, at least 30 weeks, at least 35 weeks, at least 40 weeks, at least 45 weeks, at least 50 weeks, at least 55 weeks, at least 60 weeks, at least 65 weeks, at least 70 weeks, at least 80 weeks, at least 90 weeks, or at least 100 weeks after the last injection of the treatment regimen. In an aspect, a subject does not develop any new common warts within the same anatomical area of the resolved common wart. In one aspect, a subject does not develop any new common warts at the same site as the resolved common wart.

In an aspect, a method for reducing the level of a cytokine biomarker in a subject in need thereof, the method comprises administering one or more intralesional injections to the subject of an amount of a pharmaceutical composition at a cumulative dose of from about 0.5 units of potency to about 10 units of potency, where the pharmaceutical composition comprises a filtered extract of *Candida albicans* and secreted antigens. In one aspect, a cytokine biomarker is an inflammatory cytokine. In an aspect, a subject is diagnosed with at least one common wart. In an aspect, a cytokine biomarker is selected from the group consisting of IL-23, IL-7, and IP-10. In an aspect, the level of a cytokine biomarker in a subject is reduced upon administration of a pharmaceutical composition of the present disclosure at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency. In an aspect, the level of a cytokine biomarker in a subject is reduced upon administration of a pharmaceutical composition of the present disclosure at a cumulative dose of at least about 0.5 unit of potency, at least about 1 unit of potency, at least about 2 units of potency, at least about 3 units of potency, at least about 4 units of potency, at least about 5 units of potency, at least about 6 units of potency, at least about 7 units of potency, at least about 8 units of potency, at least about 9 units of potency, or at least about 10 units of potency. In an aspect, the level of a cytokine biomarker in a subject is reduced upon administration of a pharmaceutical composition of the present disclosure at a cumulative dose from about 0.5 unit of potency to about 10 units of potency, such as from about 0.5 unit of potency to about 9.5 units of potency, from about 1 unit of potency to about 9.5 units of potency, from about 1.5 units of potency to about 9 units of potency, from about 2 units of potency to about 9 units of potency, from about 2 units of potency to about 8.5 units of potency, from about 2.5 units of potency to about 8.5 units of potency, from about 2.5 units of potency to about 8 units of potency, from about 3 units of potency to about 8 units of potency, from about 3 units of potency to about 7.5 units of potency, from about 3.5 units of potency to about 7.5 units of potency, from about 3.5 units of potency to about 7 units of potency, from about 4 units of potency to about 7 units of potency, from about 4 units of potency to about 6.5 units of potency, from about 4.5 units of potency to about 6.5 units of potency, from about 4.5 units of potency to about 6 units of potency, or from about 5 units of potency to about 6 units of potency. In an aspect, the level of a cytokine biomarker level is reduced up to 99.9% in a subject upon administration of a cumulative dose of a pharmaceutical composition of the present disclosure, such as up to 99.5%, up to 99%, up to 98%, up to 95%, up to 90%, up to 85%, up to 80%, up to 75%, up to 70%, up to 65%, up to 60%, up to 55%, up to 50%, up to 45%, up to 40%, up to 35%, up to 30%, up to 25%, up to 20%, up to 15%, up to 10%, or up to 5%. In one aspect, the level of a cytokine biomarker level is reduced from about 5% to about 99.9% in a subject upon administration of a cumulative dose of a pharmaceutical composition of the present disclosure, such as from about 5% to about 99.8%, from about 5% to about 99.5%, from about 5% to about 99%, from about 5% to about 98%, from about 5% to about 95%, from about 10% to about 95%, from about 10% to about 90%, from about 15% to about 90%, from about 15% to about 85%, from about 20% to about 85%, from about 20% to about 80%, from about 25% to about 80%, from about 25% to about 75%, from about 30% to about 75%, from about 30% to about 70%, from about 35% to about 70%, from about 35% to about 65%, from about 40% to about 65%, from about 40% to about 60%, from about 45% to about 60%, from about 45% to about 55%, or from about 50% to about 55%.

In an aspect, a method for reducing the level of IL-23 in a subject I need thereof is provided, the method comprises administering one or more intralesional injections to the subject of an amount of a pharmaceutical composition at a cumulative dose of 1 unit of potency, where the pharmaceutical composition comprises a filtered extract of *Candida albicans* and secreted antigens. In an aspect, a subject is diagnosed with at least one common wart. In one aspect, a method of the present disclosure reduces the level of IL-23 for at least about 15% in a subject upon receipt of a cumulative dose of a pharmaceutical composition of the present disclosure when compared to a level of IL-23 measured in the subject before the administering step. In one aspect, a method of the present disclosure reduces the level of IL-23 for at least about 35% in a subject upon receipt of a cumulative dose of a pharmaceutical composition of the present disclosure when compared to a level of IL-23 measured in the subject before the administering step.

In an aspect, a method for completely resolving a common wart in a subject in need thereof is provided, the method comprises reducing the level of IL-23 by at least about 35% in a subject in need thereof. In an aspect, a method for completely resolving a common wart in a subject in need thereof is provided, the method comprises reducing the level of IL-23 by at least about 15% in a subject in need thereof. In one aspect, a method of the present disclosure reduces the level of IL-23 by administering one or more intralesional injections to the subject of an amount of a pharmaceutical composition at a cumulative dose of 3 units of potency, where the pharmaceutical composition comprises a filtered extract of *Candida albicans* and secreted antigens.

In an aspect, a method for reducing the level of IL-7 in a subject in need thereof is provided, the method comprises administering one or more intralesional injections to the subject of an amount of a pharmaceutical composition at a cumulative dose of 0.6 units of potency, where the pharmaceutical composition comprises a filtered extract of *Candida albicans* and secreted antigens. In an aspect, a subject is diagnosed with at least one common wart. In one aspect, a method of the present disclosure reduces the level of IL-7 for at least about 10% in a subject upon receipt of a cumulative dose of a pharmaceutical composition of the present disclosure when compared to a level of IL-7 measured in the subject before the administering step.

In an aspect, a method for reducing the level of IL-7 in a subject in need thereof is provided, the method comprises administering one or more intralesional injections to the subject of an amount of a pharmaceutical composition at a cumulative dose of 3 units of potency, where the pharmaceutical composition comprises a filtered extract of *Candida albicans* and secreted antigens. In an aspect, a subject is diagnosed with at least one common wart. In one aspect, a method of the present disclosure reduces the level of IL-7 for at least about 20% in the subject upon receipt of a cumulative dose of a pharmaceutical composition of the present disclosure when compared to a level of IL-7 measured in the subject before the administering step.

In an aspect, a method for reducing the level of IP-10 in a subject in need thereof is provided, the method comprises administering one or more intralesional injections to the subject of an amount of a pharmaceutical composition at a cumulative dose of 3 units of potency, where the pharmaceutical composition comprises a filtered extract of *Candida albicans* and secreted antigens. In an aspect, a subject is diagnosed with at least one common wart. In one aspect, a method of the present disclosure reduces the level of IP-10 for at least about 5% in the subject upon receipt of a cumulative dose of a pharmaceutical composition of the present disclosure when compared to a level of IP-10 measured in the subject before the administering step.

In an aspect, methods of the present disclosure are effective at achieving a treatment goal at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency. In one aspect, methods of the present disclosure are capable of achieving a treatment goal at a cumulative dose of less than about 0.5 unit of potency, less than about 1 unit of potency, less than about 2 units of potency, less than about 3 units of potency, less than about 4 units of potency, less than about 5 units of potency, less than about 6 units of potency, less than about 7 units of potency, less than about 8 units of potency, less than about 9 units of potency, or less than about 10 units of potency.

In an aspect, methods of the present disclosure are effective at achieving a treatment goal at a cumulative dose of at least about 0.5 unit of potency, at least about 1 unit of potency, at least about 2 units of potency, at least about 3 units of potency, at least about 4 units of potency, at least about 5 units of potency, at least about 6 units of potency, at least about 7 units of potency, at least about 8 units of potency, at least about 9 units of potency, or at least about 10 units of potency. In one aspect, methods of the present disclosure are capable of achieving a treatment goal at a cumulative dose of at least about 0.5 unit of potency, at least about 1 unit of potency, at least about 2 units of potency, at least about 3 units of potency, at least about 4 units of potency, at least about 5 units of potency, at least about 6 units of potency, at least about 7 units of potency, at least about 8 units of potency, at least about 9 units of potency, or at least about 10 units of potency.

In an aspect, methods of the present disclosure are effective at achieving a treatment goal at a cumulative dose from about 0.5 unit of potency to about 10 units of potency, such as from about 0.5 unit of potency to about 9.5 units of potency, from about 1 unit of potency to about 9.5 units of potency, from about 1.5 units of potency to about 9 units of potency, from about 2 units of potency to about 9 units of potency, from about 2 units of potency to about 8.5 units of potency, from about 2.5 units of potency to about 8.5 units of potency, from about 2.5 units of potency to about 8 units of potency, from about 3 units of potency to about 8 units of potency, from about 3 units of potency to about 7.5 units of potency, from about 3.5 units of potency to about 7.5 units of potency, from about 3.5 units of potency to about 7 units of potency, from about 4 units of potency to about 7 units of potency, from about 4 units of potency to about 6.5 units of potency, from about 4.5 units of potency to about 6.5 units of potency, from about 4.5 units of potency to about 6 units of potency, or from about 5 units of potency to about 6 units of potency. In an aspect, methods of the present disclosure are capable of achieving aa treatment goal at a cumulative dose from about 0.5 unit of potency to about 10 units of potency, such as from about 0.5 unit of potency to about 9.5 units of potency, from about 1 unit of potency to about 9.5 units of potency, from about 1.5 units of potency to about 9 units of potency, from about 2 units of potency to about 9 units of potency, from about 2 units of potency to about 8.5 units of potency, from about 2.5 units of potency to about 8.5 units of potency, from about 2.5 units of potency to about 8 units of potency, from about 3 units of potency to about 8 units of potency, from about 3 units of potency to about 7.5 units of potency, from about 3.5 units of potency to about 7.5 units of potency, from about 3.5 units of potency to about 7 units of potency, from about 4 units of potency to about 7 units of potency, from about 4 units of potency to about 6.5 units of potency, from about 4.5 units of potency to about 6.5 units of potency, from about 4.5 units of potency to about 6 units of potency, or from about 5 units of potency to about 6 units of potency.

In an aspect, each dose administered in the methods of the present disclosure can be administered via a form selected from the group consisting of oral, buccal, sublingual, topical, injectable, infused, inhalable, rectal, intravenous, intramuscular, and subcutaneous forms. In an aspect, two or more intralesional injections are provided to a subject in need thereof over a period of time. In an aspect, each dose has a potency of at least 0.3 unit of potency. In one aspect, each dose has a potency of at least 0.5 unit of potency. In an aspect, each dose is administered at a dose of at least about 0.1 unit of potency to about 1 unit of potency, such as about 0.1 unit of potency to about 0.9 unit of potency, such as about 0.2 unit of potency to about 1 unit of potency, such as about 0.2 unit of potency to about 0.8 unit of potency, such as about 0.2 unit of potency to about 0.5 unit of potency, such as about 0.2 unit of potency to about 0.4 unit of potency, such as about 0.3 unit of potency to about 0.7 unit of potency, or such as about 0.4 unit of potency to about 0.6 unit of potency. In an aspect, each dose is provided at a volume of from about 5 μL to about 500 μL, such as from about 5 μL to about 450 μL, from about 5 μL to about 400 μL, from about 5 μL to about 350 μL, from about 5 μL to about 300 μL, from about 5 μL to about 250 μL, from about 5 μL to about 200 μL, from about 5 μL to about 150 μL, from about 5 μL to about 100 μL, from about 5 μL to about 50 μL, from about 5 μL to about 40 μL, from about 5 μL to about 30 μL, from about 5 μL to about 20 μL, from about 5 μL to about 10 μL, from about 50 μL to about 500 μL, from about 50 μL to about 450 μL, from about 50 μL to about 400 μL, from about 50 μL to about 350 μL, from about 50 μL to about 300 μL, from about 50 μL to about 250 μL, from about 50 μL to about 200 μL, from about 50 μL to about 150 μL, from about 50 μL to about 100 μL, from about 100 μL to about 500 μL, from about 150 μL to about 450 μL, from about 200 μL to about 400 μL, or from about 250 μL to about 350 μL. In one aspect, a pair of doses are provided about two weeks apart to a subject in need thereof, such as 10 days, 11 days, 12 days, 13 days, 14 days, 15 days, 16 days, 17 days, or 18 days apart. In an aspect, a pair of doses are provided about three weeks apart to a subject in need thereof, such as 17 days, 18 days, 19 days, 20 days, 21 days, 22 days, 23 days, 24 days, or 25 days apart. In an aspect, doses administered in the methods are provided to a subject in need thereof over a period of about 2 weeks to about 27 weeks, such as about 2 weeks to about 26 weeks, such as about 2 weeks to about 25 weeks, such as about 2 weeks to about 24 weeks, such as about 2 weeks to about 23 weeks, such as about 2 weeks to about 22 weeks, such as about 2 weeks to about 21 weeks, such as about 2 weeks to about 20 weeks, such as about 2 weeks to about 19 weeks, such as about 2 weeks to about 18 weeks, such as about 2 weeks to about 17 weeks, such as about 2 weeks to about 16 weeks, such as about 2 weeks to about 15 weeks, such as about 2 weeks to about 14 weeks, such as about 2 weeks to about 13 weeks, such as about 2 weeks to about 12 weeks, such as about 2 weeks to about 11 weeks, such as about 2 weeks to about 10 weeks, such as about 2 weeks to about 9 weeks, such as about 2 weeks to about 8 weeks, such as about 2 weeks to about 7 weeks, such as about 2 weeks to about 6 weeks, such as about 2 weeks to about weeks, such as about 2 weeks to about 4 weeks, or such as about 2 weeks to about 3 weeks. In an aspect, doses administered in the methods are provided to a subject in need thereof over a period of about 3 weeks to about 27 weeks, such as about 4 weeks to about 27 weeks, about 5 weeks to about 27 weeks, about 6 weeks to about 27 weeks, about 7 weeks to about 27 weeks, about 8 weeks to about 27 weeks, about 9 weeks to about 27 weeks, about 10 weeks to about 27 weeks, about 11 weeks to about 27 weeks, about 12 weeks to about 27 weeks, about 13 weeks to about 27 weeks, about 14 weeks to about 27 weeks, about 15 weeks to about 27 weeks, about 16 weeks to about 27 weeks, about 17 weeks to about 27 weeks, about 18 weeks to about 27 weeks, about 19 weeks to about 27 weeks, about 20 weeks to about 27 weeks, about 21 weeks to about 27 weeks, about 22 weeks to about 27 weeks, about 23 weeks to about 27 weeks, about 24 weeks to about 27 weeks, about 25 weeks to about 27 weeks, or about 26 weeks to about 27 weeks. In one aspect, doses administered in the methods are provided to a subject in need thereof over a period of about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, or about 27 weeks.

In an aspect, an intralesional injection is provided to a subject in need thereof. In one aspect, an intralesional injection is provided at the perimeter of a common wart being treated. In an aspect, an intralesional injection is provided near the perimeter of a common wart being treated. In one aspect, an intralesional injection is provided at a location that is about 5 mm or less from the peripheral margin of a common wart being treated, such as about 4 mm or less, about 3 mm or less, about 2 mm or less, or about 1 mm or less from the peripheral margin of a common wart. In one aspect, a perimeter is defined by the peripheral margin of a wart. In an aspect, an intralesional injection is provided to the common wart being treated. In one aspect, an intralesional injection is provided to the largest common wart within an anatomical area, in the presence of a plurality of common warts in the same anatomical area. In one aspect, an intralesional injection is provided to the largest common wart within an anatomical area, in the presence of a plurality of common warts in the same anatomical area and a non-common wart. In an aspect, the largest common wart is determined by choosing the common wart within an anatomical area having the largest diameter.

In an aspect, a subject has a common wart measuring between about 3 mm to about 20 mm prior to beginning of a treatment of the present disclosure, such as between about 3 mm to about 19 mm, between about 4 mm to about 20 mm, between about 4 mm to about 19 mm, between about 5 mm to about 19 mm, between about 5 mm to about 18 mm, between about 6 mm to about 18 mm, between about 6 mm to about 17 mm, between about 7 mm to about 16 mm, between about 7 mm to about 15 mm, between about 8 mm to about 15 mm, between about 8 mm to about 14 mm, between about 9 mm to about 14 mm, between about 9 mm to about 13 mm, between about 10 mm to about 13 mm, between about 10 mm to about 12 mm, or between about 11 mm to about 12 mm. In an aspect, a subject has a common wart measuring between about 20 mm to about 1 cm, such as between about 20 mm to about 95 mm, such as between about 25 mm to about 1 cm, such as between about 20 mm to about 90 mm, such as between about 25 mm to about 95 mm, such as between about 25 mm to about 90 mm, such as between about 30 mm to about 90 mm, such as between about 30 cm to about 85 mm, such as between about 35 mm to about 85 mm, such as between about 35 mm to about 80 mm, such as between about 40 mm to about 80 mm, such as between about 40 mm to about 75 mm, such as between about 45 mm to about 75 mm, such as between about 45 mm to about 60 mm, such as between about 50 mm to about 70 mm, such as between about 50 mm to about 65 mm, such as between about 55 mm to about 65 mm, or such as between about 55 mm to about 60 mm. In an aspect, a subject has a common wart measuring between about 1 cm to about 100 cm, such as between about 1 cm to about 95 cm, between about 5 cm to about 100 cm, between about 5 cm to about 95 cm, between about 10 cm to about 95 cm, between about 10 cm to about 90 cm, between about 15 cm to about 90 cm, between about 15 cm to about 85 cm, between about 20 cm to about 85 cm, between about 20 cm to about 80 cm, between about 25 cm to about 80 cm, between about 25 cm to about 75 cm, between about 30 cm to about 75 cm, between about 30 cm to about 70 cm, between about 35 cm to about 70 cm, between about 35 cm to about 65 cm, between about 40 cm to about 65 cm, between about 40 cm to about 60 cm, between about 45 cm to about 60 cm, between about 45 cm to about 55 cm, or between about 50 cm to about 55 cm.

In an aspect, two or more intralesional injections are provided to a subject in need thereof over a period of time. In one aspect, each of the two or more intralesional injection is provided at a dose of at least 0.5 unit of potency. In an aspect, each of the two or more intralesional injection is provided at a dose of at least about 0.1 unit of potency to about 1 unit of potency, such as about 0.1 unit of potency to about 0.9 unit of potency, such as about 0.2 unit of potency to about 1 unit of potency, such as about 0.2 unit of potency to about 0.8 unit of potency, such as about 0.3 unit of potency to about 0.7 unit of potency, or such as about 0.4 unit of potency to about 0.6 unit of potency. In an aspect, each of the two or more intralesional injection is provided at a volume of from about 5 µL to about 500 µL, such as from about 5 µL to about 450 µL, from about 5 µL to about 400 µL, from about 5 µL to about 350 µL, from about 5 µL to about 300 µL, from about 5 µL to about 250 µL, from about 5 µL to about 200 µL, from about 5 µL to about 150 µL, from about 5 µL to about 100 µL, from about 5 µL to about 50 µL, from about 5 µL to about 40 µL, from about 5 µL to about 30 µL, from about 5 µL to about 20 µL, from about 5 µL to about 10 µL, from about 50 µL to about 500 µL, from about 50 µL to about 450 µL, from about 50 µL to about 400 µL, from about 50 µL to about 350 µL, from about 50 µL to about 300 µL from about 50 µL to about 250 µL, from about 50 µL to about 200 µL, from about 50 µL to about 150 µL, from about 50 µL to about 100 µL, from about 100 µL to about 500 µL, from about 150 µL to about 450 µL, from about 200 µL to about 400 µL, or from about 250 µL to about 350 µL.

In one aspect, a pair of intralesional injections in two or more intralesional injections are provided about two weeks apart to a subject in need thereof, such as 10 days, 11 days, 12 days, 13 days, 14 days, 15 days, 16 days, 17 days, or 18 days apart. In an aspect, a pair of intralesional injections in two or more intralesional injections are provided about three weeks apart to a subject in need thereof, such as 17 days, 18 days, 19 days, 20 days, 21 days, 22 days, 23 days, 24 days, or 25 days apart.

In an aspect, two or more intralesional injections are provided to a subject in need thereof over a period of about 2 weeks to about 27 weeks, such as about 2 weeks to about 26 weeks, such as about 2 weeks to about 25 weeks, such as about 2 weeks to about 24 weeks, such as about 2 weeks to about 23 weeks, such as about 2 weeks to about 22 weeks, such as about 2 weeks to about 21 weeks, such as about 2 weeks to about 20 weeks, such as about 2 weeks to about 19 weeks, such as about 2 weeks to about 18 weeks, such as about 2 weeks to about 17 weeks, such as about 2 weeks to about 16 weeks, such as about 2 weeks to about 15 weeks, such as about 2 weeks to about 14 weeks, such as about 2 weeks to about 13 weeks, such as about 2 weeks to about 12 weeks, such as about 2 weeks to about 11 weeks, such as about 2 weeks to about 10 weeks, such as about 2 weeks to about 9 weeks, such as about 2 weeks to about 8 weeks, such as about 2 weeks to about 7 weeks, such as about 2 weeks to about 6 weeks, such as about 2 weeks to about 5 weeks, such as about 2 weeks to about 4 weeks, or such as about 2 weeks to about 3 weeks. In an aspect, two or more intralesional injections are provided to a subject in need thereof over a period of about 3 weeks to about 27 weeks, such as about 4 weeks to about 27 weeks, about 5 weeks to about 27 weeks, about 6 weeks to about 27 weeks, about 7 weeks to about 27 weeks, about 8 weeks to about 27 weeks, about 9 weeks to about 27 weeks, about 10 weeks to about 27 weeks, about 11 weeks to about 27 weeks, about 12 weeks to about 27 weeks, about 13 weeks to about 27 weeks, about 14 weeks to about 27 weeks, about 15 weeks to about 27 weeks, about 16 weeks to about 27 weeks, about 17 weeks to about 27 weeks, about 18 weeks to about 27 weeks, about 19 weeks to about 27 weeks, about 20 weeks to about 27 weeks, about 21 weeks to about 27 weeks, about 22 weeks to about 27 weeks, about 23 weeks to about 27 weeks, about 24 weeks to about 27 weeks, about 25 weeks to about 27 weeks, or about 26 weeks to about 27 weeks. In one aspect, two or more intralesional injections are provided to a subject in need thereof over a period of about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, or about 27 weeks.

In one aspect, two or more intralesional injections are provided to a subject in need thereof in two or more subgroups of intralesional injections over a period of time. In one aspect, each of the subgroup of two or more subgroups is provided at a dose of at least 0.5 unit of potency. In an aspect, each of the subgroup of the two or more subgroups is provided at a dose of at least about 0.1 unit of potency to about 1 unit of potency, such as about 0.1 unit of potency to about 0.9 unit of potency, such as about 0.2 unit of potency to about 1 unit of potency, such as about 0.2 unit of potency to about 0.8 unit of potency, such as about 0.3 unit of potency to about 0.7 unit of potency, or such as about 0.4 unit of potency to about 0.6 unit of potency. In an aspect, each of the subgroup of the two or more subgroups is provided at a volume of from about 5 µL to about 500 µL, such as from about 5 µL to about 450 µL, from about 5 µL to about 400 µL, from about 5 µL to about 350 µL, from about 5 µL to about 300 µL, from about 5 µL to about 250 µL, from about 5 µL to about 200 µL, from about 5 µL to about 150 µL, from about 5 µL to about 100 µL, from about 5 µL to about 50 µL, from about 5 µL to about 40 µL, from about 5 µL to about 30 µL, from about 5 µL to about 20 µL, from about 5 µL to about 10 µL, from about 50 µL to about 500 µL, from about 50 µL to about 450 µL, from about 50 µL to about 400 µL, from about 50 µL to about 350 µL, from about 50 µL to about 300 µL, from about 50 µL to about 250 µL, from about 50 µL to about 200 µL, from about 50 µL to about 150 µL, from about 50 µL to about 100 µL, from about 100 µL to about 500 µL, from about 150 µL to about 450 µL, from about 200 µL to about 400 µL, or from about 250 µL to about 350 µL.

In an aspect, a pair of subgroups within two or more subgroups of intralesional injections are provided about two weeks apart to a subject in need thereof, such as 10 days, 11 days, 12 days, 13 days, 14 days, 15 days, 16 days, 17 days, or 18 days apart. In one aspect, a pair of subgroups within two or more subgroups of intralesional injections are provided about three weeks apart to a subject in need thereof, such as 17 days, 18 days, 19 days, 20 days, 21 days, 22 days, 23 days, 24 days, or 25 days apart.

In an aspect, a subgroup of intralesional injections comprises at least two intralesional injections such as two intralesional injections, three intralesional injections, four intralesional injections, five intralesional injections, six intralesional injections, seven intralesional injections, eight intralesional injections, nine intralesional injections, or ten intralesional injections.

In one aspect, intralesional injections within a subgroup of intralesional injections are administered at approximately the same time, such as within about 1 minute, within about 2 minutes, within about 3 minutes, within about 4 minutes, within about 5 minutes. In one aspect, intralesional injections within a subgroup of intralesional injections are administered are administered within 24 hours, such as within about 18 hours, within about 12 hours, within about 6 hours, within about 5 hours, within about 4 hours, within about 3 hours, within about 2 hours, or within about 1 hour.

In one aspect, intralesional injections within a subgroup of intralesional injections are provided around a common wart being treated. In an aspect, intralesional injections within a subgroup of intralesional injections are evenly spaced apart near the perimeter of a common wart being treated. In one aspect, each of the intralesional injection within a subgroup of intralesional injections is provided at a location that is about 5 mm or less from the peripheral margin of a common wart being treated, such as about 4 mm or less, about 3 mm or less, about 2 mm or less, or about 1 mm or less from the peripheral margin of a common wart. In an aspect, intralesional injections within a subgroup of intralesional injections are evenly spaced apart at the perimeter of a common wart being treated. In one aspect, a perimeter is defined by the peripheral margin of a wart.

In an aspect, a pharmaceutical composition administered by a method of the present disclosure comprises a filtered extract of two strains of *Candida albicans* and secreted antigens, where a representative sample of a first strain has been deposited with the ATCC under ATCC Accession No. PTA-126019, and a representative sample of a second strain has been deposited with the ATCC under ATCC Accession No. PTA-126020. In an aspect, a representative sample of a first strain has been deposited with the ATCC under ATCC Accession No. ATCC-10231.

In an aspect, a subject being treated with the methods of the present disclosure is between the ages of 18 and 65, such as between 20 and 60, between 18 and 30, between 25 and 50, between 30 and 40, between 40 to 50, or between 50 to 65. In one aspect, a subject being treated with the methods of the present disclosure is a pediatric patient. In one aspect, a pediatric patient is a premature newborn. In an aspect, a pediatric patient is a term newborn. In one aspect, a pediatric patient is a neonate. In one aspect, a pediatric patient is an infant. In an aspect, a pediatric patient is a toddler. In one aspect, a pediatric patient is a young child. In one aspect, a pediatric patient is a child. In an aspect, a pediatric patient is an adolescent. In an aspect, a pediatric patient is a child patient below about 18, 15, 12, 10, 8, 6, 4, 3, 2, or 1 years old. In one aspect, a subject being treated with the methods of the present disclosure was diagnosed with a first common wart at least 12 weeks prior to receiving one or more intralesional injections, such as between 12 weeks to 100 weeks, between 15 weeks to 90 weeks, between 20 to 80 weeks, between 25 to 75 weeks, between 30 to 70 weeks, between 35 to 65 weeks, between to 60 weeks, between 45 to 55 weeks, or between 50 to 55 weeks. In an aspect, a subject being treated with the methods of the present disclosure was not diagnosed with a recalcitrant wart. In an aspect, a recalcitrant wart is a wart that was not successfully treated by prior treatment, excluding over-the-counter treatments. In one aspect, a recalcitrant wart is a wart that was not successfully treated by one or more types of prior treatment, such as two or more, three or more, four or more, five or more, six or more, seven or more, eight or more, nine or more, or ten or more types of prior treatment. In an aspect, an over-the-counter treatment is a medication sold directly to a consumer without a prescription from a healthcare professional.

In an aspect, a subject being treated with the methods of the present disclosure has a baseline result of between 5 mm and 25 mm to the Delayed Type Hypersensitivity (DTH) test. In one aspect, a DTH test is performed by administering a single intradermal injection of CANDIN® (0.1 mL; Allermed/Nielsen Biosciences) on the volar surface of the forearm or on the outer aspect of the upper arm, at least 2 cm away from any primary injectable warts. The skin is cleansed with 70% alcohol before applying the skin test. The intradermal injection is given as superficially as possible causing a distinct, sharply defined bleb. The test is read at 48±4 hours post the DTH challenge injection, by visually inspecting the test site and palpating the indurated area. Measurements are made across two diameters. The mean of the longest and the midpoint orthogonal diameters of the indurated area is reported as the DTH response.

In an aspect, a subject being treated with the methods of the present disclosure is not diagnosed with a systematic disease that compromises immune function. In an aspect, a subject being treated with the methods of the present disclosure is not diagnosed with a localized disease that compromises immune function. In an aspect, a subject being treated with the methods of the present disclosure is not diagnosed with a systematic condition that compromises immune function. In an aspect, a subject being treated with the methods of the present disclosure is not diagnosed with a localized condition that compromises immune function. In an aspect, a subject being treated with the methods of the present disclosure is not diagnosed with psoriasis. In an aspect, a subject being treated with the methods of the present disclosure is not receiving a treatment resulting in being immunocompromised.

In an aspect, a subject being treated with the methods of the present disclosure has not been diagnosed with diabetes mellitus. In an aspect, a subject being treated with the methods of the present disclosure does not have a history of keloid formation. In an aspect, a subject being treated with the methods of the present disclosure does not have an existing dermatologic condition in the same anatomical area as the wart being treated. In an aspect, a subject being treated with the methods of the present disclosure does not have an underlying inflammatory condition. In an aspect, an underlying inflammatory condition is an arthritic joint.

In an aspect, a subject being treated with the methods of the present disclosure has not received one or more treatments selected from the group consisting of liquid nitrogen, carbon dioxide, electrodessication, laser, surgery, simple occlusion (e.g. duct tape), salicylic or related acids including trichloroacetic acid and bichloroacetic acid, over-the-counter treatments, and cantharidin, within 4 weeks prior to the administering step. In an aspect, a subject being treated with the methods of the present disclosure has not received one or more immunotherapy selected from the group consisting of diphenylcyclopropenone (DPCP), dinitrochlorobenzene (DNCB), imiquimod, 5-florouracil, bleomycin, and podophyllin, within 12 weeks prior to the administering step. In an aspect, a subject being treated with the methods of the present disclosure has not received one or more systematic treatment selected from the group consisting of cimetidine, zinc supplements at a dose higher than 20 mg of elemental zinc daily, azathioprine, 6-mercaptopurine, methotrexate, infliximab, adalimumab, etanercept, and steroid, within 12 weeks prior to the administering step. In an aspect, a subject being treated with the methods of the present disclosure has not received any investigational agent within 30 days prior to the administering step. In an aspect, a subject being treated with the methods of the present disclosure has not received any investigational agent within 5 half-lives of said investigational agent prior to the administering step.

EXAMPLES

Example 1—Production of a Composition Comprising a Sterile Filtrate of Candida albicans and Secreted Antigens First, a pre-production culture is prepared from an oil-covered stock culture by aseptically removing one loopful of the stock culture of each two strains of Candida albicans (ATCC Accession Nos. PTA-126019 and PTA-126020) and placing it in Animal Free Trypticase Soy Broth (ATSB; TechNova, Dartmouth, Nova Scotia). This pre-production culture is incubated at 20-25° C. until a growth pellet is observed at the bottom of the tube, usually within 7 to 14 days. After evidence of fungal growth (e.g. milky yeast-like growth on the bottom of the tube) is observed, a portion of the growth is transferred to a plate of Animal Free Trypticase Soy Agar (ATSA; TechNova, Dartmouth, Nova Scotia) and is incubated at 20-25° C. for 3 to 7 days. The growth from the ATSA plate is subcultured to a fresh ATSA plate and the plate is streaked to produce isolated colonies. The ATSA plate is incubated at 20-25° C. for 3 to 7 days.

Figure 2:
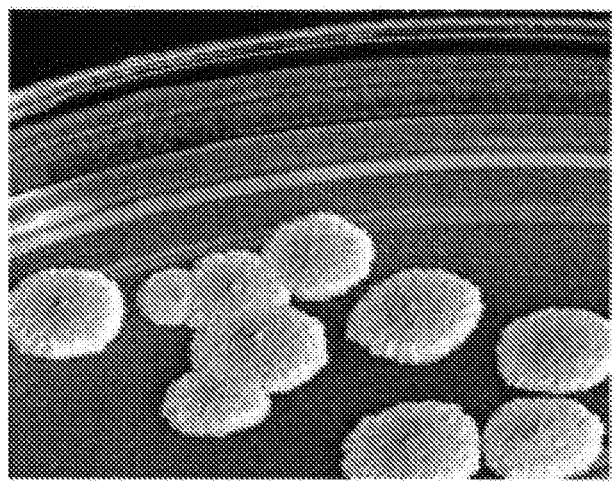
FIG. 2 shows characteristic morphology of isolated colonies of a second strain of *Candida albicans*, deposited as ATCC Accession No. PTA-126020, in accordance with the present disclosure.

From the ATSA plate, several isolated colonies with characteristic morphology (see FIG. 1 and FIG. 2 show characteristic morphologies of isolated colonies of a first strain and a second strain, respectively) are transferred to an Erlenmeyer flask containing Chemically Defined Candida Medium (CDCM; TechNova, Dartmouth, Nova Scotia). CDCM consists of 3.6 g/L $KH_2PO_4$, 1.2 g/L $Na_2HPO_4$, 8.0 g/L $(NH_4)_2SO_4$, 0.2 g/L $MgSO_4 \cdot 7H_2O$, 0.01 g/L $ZnSO_4 \cdot 7H_2O$, 8.0 g/L sucrose, and 0.01 g/L biotin. The Erlenmeyer flask is incubated 3-7 days on a shaker set at approximately 60 rpm at a temperature of 20-25° C. Referring to FIG. 1, an isolated colony of a first strain deposited as ATCC Accession No. PTA-126019 appears as pasty cream colored with smooth entire margins. Referring to FIG. 2, an isolated colony of a second strain deposited as ATCC Accession No. PTA-126020 appears as white cream-colored having a somewhat rough surface and irregular margins.

Figure 3:
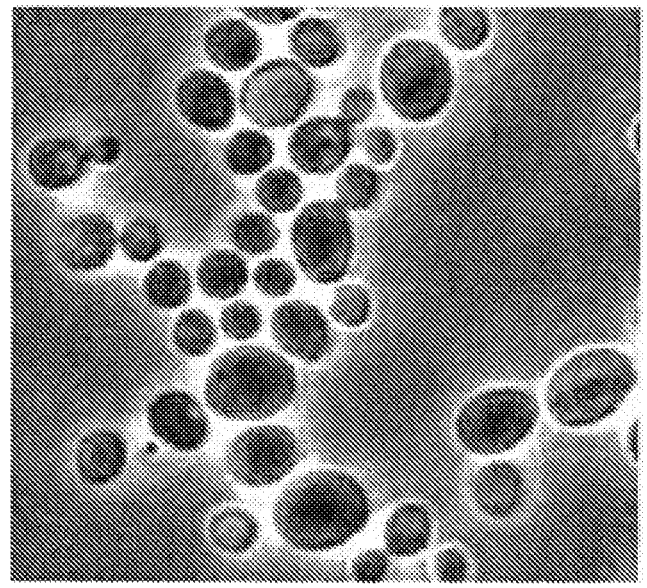
FIG. 3 shows typical appearance of budding yeast cells of *Candida albicans* in accordance with the present disclosure.
Figure 4:
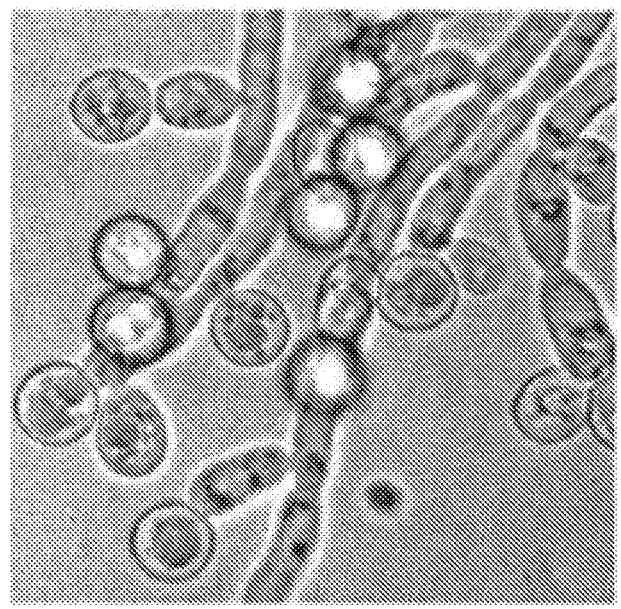
FIG. 4 shows typical appearance of pseudohyphae of *Candida albicans* in accordance with the present disclosure.

When the inoculum shows budding yeast pseudohyphae (see FIG. 3 for an illustration of budding yeast cells of Candida albicans and FIG. 4 for pseudohyphae of Candida albicans) and if it is free of bacteria, each of the stock is transferred to separate production flasks containing CDCM at a dilution of approximately 1:100. For example, approximately 1.0 mL of each of the stock is transferred to separate production flasks containing 100 mL CDCM; or approximately 10 mL of each of the stock is transferred to separate production flasks containing 1000 mL CDCM. The production flasks are incubated at 20-25° C. for 7 days on a shaker, set at 60 rotations or oscillations per minute.

Upon completion of incubation, 1.0 mL of 1% phenol is added to each production flasks. The flasks are stored at 20-25° C. for 7 days for the fungus to be killed. The contents of all production flasks containing acceptable growth and no contamination are then pooled in a sterile glass bottle. The pooled material is cultured by adding 1.0 mL to each of three 40 mL tubes of Trypticase Soy Broth (TSB; TechNova, Dartmouth, Nova Scotia). Each TSB culture is further diluted 10-fold in TSB and is incubated at 20-25° C. for 7 days to ensure non-viability. During the culturing period, the poled production material is stored in a holding bottle at 20-25° C. for 7 days.

Dialyze the pooled culture in USP grade Water for Injection (WFI; TechNova, Dartmouth, Nova Scotia) at 1-8° C. using Spectrapor 6,000-8,000 MWCO dialysis tubing (size 40 mm). Dialyze with a 20-fold volume of WFI and repeat the procedure twice at 24-hour intervals. The dialyzed material is then heated uniformly for 60 minutes at 90-95° C. in a water bath.

200 mL of the heat treated dialyzed material is added to a 600 mL lyophilization flask and freeze dried in a Labconco lyophilizer. This procedure is repeated until the entire lot has been lyophilized. Lyophilized material is then covered with petroleum ether at 20-25° C. for 6 to 8 hours with the supernatant being discarded via filtration. The resulting material is air dried in a fume hood. This is the dry powder denoted as the source material for further processing.

Dilute the source material with Coca's Glycerol Solution (0.25% NaCl, 0.125% $NaHCO_3$, 53% glycerin; 47% WFI) having a pH in the range of 6 to 8.5 at a desired weight by volume extraction ratio. In an aspect, a volume extraction ratio is 1:20 w/v, where 20 mL of Coca's Glycerol Solution is added to per gram of source material. This extract is mixed intermittently for approximately 71 hours on a magnetic stirrer at 1-8° C. until the source material appears homogenous throughout the mixture.

The extract is then centrifuged at approximately 4000 RPMs for 20 minutes. After that, the extract is filtered by vacuum filtration with a Buchner funnel and Whatman No. 3 filter paper. Adjust the filtered extract to have a final concentration of 0.4% phenol and return it to 1-8° C. A sterile Sartorius 0.2 μm filter capsule (#5231307H) and filter the product under a class 100 laminar flow hood in a class 100,000 room.

In a sterile filtration room, use a sterile Sartorius "Sartobran" 0.45/0.2 μm [5235307H7OOA (0.05 $m^2$) or 5231307H5OOB (0.03 $m^2$)] to sterilize the product. Collect the filtered solution to an appropriately sized, sterile depyrogenated container, and store the filtered solution at 1-8° C. Finally, 1.7 mL of this master lot filtered solution is diluted with 998.3 mL of a diluent, which consists of 5.0 g/L NaCl, 2.5 g/L $NaHCO_3$, 4.5 mL/L phenol, 1.2 mL/L 20% solution human serum albumin, 0.8 mL/L polysorbate 80.

Example 2—Intralesional Injection to a Wart

Figure 6:
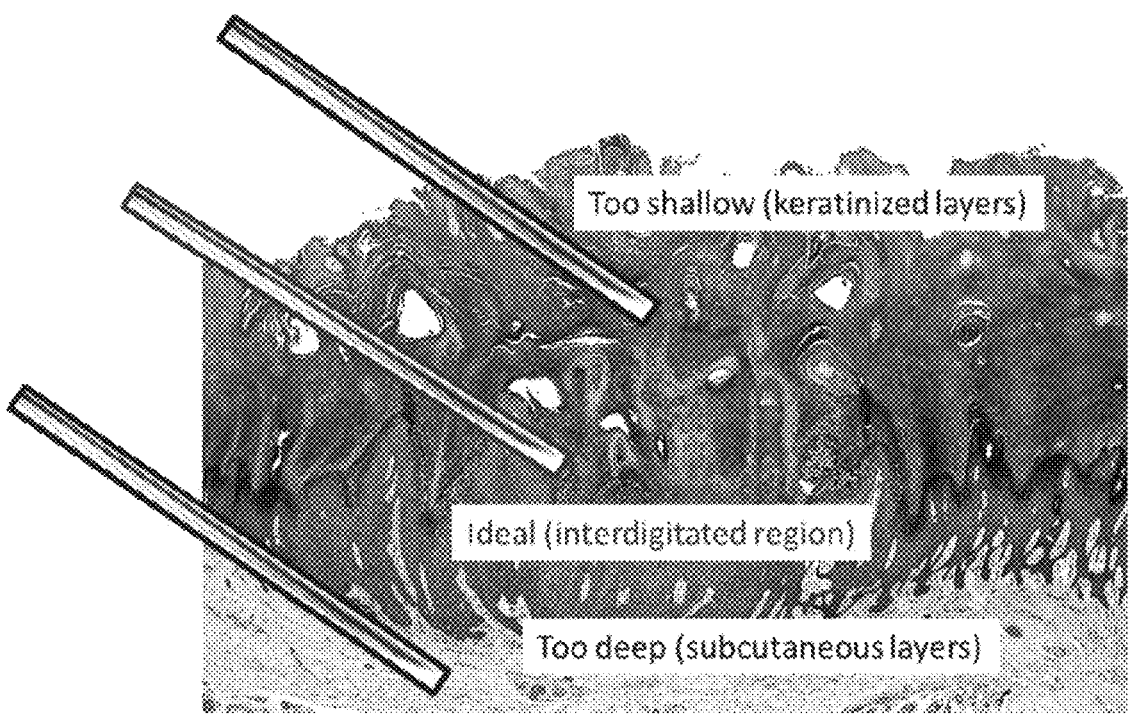
FIG. 6 illustrates the preferred location of the intralesional injection.

An intralesional injection of a pharmaceutical composition of the present disclosure to a wart is provided beneath the common wart at the region of the interdigitated base of the wart. FIG. 6 illustrates the preferred location of the intralesional injection. Preferably, a blanching of the treated wart is observed upon injection. Without being limited to theory, the injection is performed slowly to help the injected pharmaceutical composition to spread along the dermal epidermal junction. Most injections are performed with the bevel down. However, for particularly thick warts, the injection may be performed with the bevel of the needle aiming upwards. For particularly thin warts, the injection may be performed with the bevel of the needle aiming sideways. After the injection, moderate pressure is applied to the injected wart.

In some instances, a dose of a pharmaceutical composition can be injected via multiple injections at the interdigitated base of the wart.

Example 3—Treatment by Injections to a Single Wart

To treat a patient diagnosed with a common wart, intralesional injections of a pharmaceutical composition of the present disclosure at a dose of 0.5 unit of potency are provided to the largest common wart every second week (14±2 days) for a maximum of 10 injections. If the primary common wart exhibits a complete response, the second largest injectable common wart of all anatomical regions is injected with the same pharmaceutical composition at the same dose of 0.5 unit of potency. If an injected wart recurs after exhibiting a complete response, it is re-injected instead of the non-primary injected wart that was injected at the previous visit. This injection strategy is repeated for a maximum of 10 injections or until all injectable common warts exhibit a complete response, if it occurs before all 10 injections are used.

The above treatment is effective for completely resolving 85% of all primary injected warts at any number of injections, compared to 52% of those injected with a placebo. Moreover, 75% of all warts mapped at baseline in subjects injected with a pharmaceutical composition of the present disclosure were completely resolved, compared to 34% of those injected with a placebo. The median number of injections required to completely resolve a primary injected wart is 5 injections, compared to 10 injections of the placebo. Furthermore, at 4 months following the last injection, 50% of primary injected warts remain completely resolved, compared to 31% of those injected with a placebo.

The above treatment is also effective for resolving all common warts in 53% of the 52 subjects treated, compared to 21% of subjects receiving placebo. In patients also diagnosed with non-common warts, 75% showed resolution of non-common warts as compared to 57% receiving placebo.

Moreover, the above treatment is capable of resolving a primary injected wart previously treated with cryotherapy at a rate of 47% compared to 21% by the placebo.

10% of the subjects receiving treatment exhibited scarring at the site of a resolved wart comparing to 6% of the subjects receiving placebo. 3% of the subjects receiving treatment exhibited hypopigmentation at the site of a resolved wart comparing to 0% of the subjects receiving placebo.

Example 4—Treatment by Injections to Multiple Warts

To treat a patient diagnosed with common warts in at least 2 different anatomic regions, a pharmaceutical composition of the present disclosure is injected in the largest wart (primary) per anatomical region, for a minimum of two and a maximum of four injections of 0.3 unit of potency each per visit every second week (14±2 days) for a maximum of 10 visits with injections. No more than one wart per anatomical region is injected on any given visit. If any primary injected wart exhibits a complete response, the next largest injectable common wart is injected with the same pharmaceutical composition at the same dose of 0.3 unit of potency per injection (maximum of 4 injections per visit) providing the new injectable wart is not within the same anatomical region as other currently injected warts. If an injected wart recurs after exhibiting a complete response, it is re-injected instead of the non-primary injected wart that was injected at the previous visit. This injection strategy is repeated for a maximum total of 10 injection visits per subject or until all injectable common warts exhibit a complete response, if it occurs before the end of the 10 injection visits.

The above treatment is effective for completely resolving 82% of the largest primary injected warts at any number of injections, compared to 52% of those injected with a placebo. The median number of injections required to completely resolve the largest primary injected wart is 4 injections, compared to 10 injections of the placebo. Furthermore, at 4 months following the last injection, 43% of the largest primary injected warts remain completely resolved, compared to 31% of those injected with a placebo.

7% of the subjects receiving treatment exhibited scarring at the site of a resolved wart comparing to 6% of the subjects receiving placebo. 3% of the subjects receiving treatment exhibited hypopigmentation at the site of a resolved wart comparing to 0% of the subjects receiving placebo.

Example 5—Cytokine Biomarker Changes in Wart Patients

To evaluate biomarker changes in wart patients, intralesional injections are provided to a total of 58 subjects. A pharmaceutical composition of the present disclosure is provided intralesionally to each of 43 subjects in the largest (primary) wart every two weeks at a dose of 0.3 potency each injection for a maximum of 10 injections. On the other hand, a placebo is provided intralesionally to each of 15 subjects in the primary wart every two weeks for a maximum of 10 injections.

If the primary wart exhibited a complete response, the next largest wart is treated using the same dose. This strategy is repeated until all warts are resolved or for 10 injections, whichever was reached first. If an injected wart recurred after exhibiting a complete response, it is retreated instead of the wart injected in the previous visit.

Blood samples are collected at screening prior to initiation of treatment (V1); after treatment injections and immediately prior to the third injection (V5); and study completion, i.e., upon resolution of all warts or 10 injections (V13). Plasma separated from the blood is stored at −80° C. until assayed for multiple protein biomarkers (45-plex cytokine/chemokine/growth factor panel) by BioAgilytix (Durham, NC).

Individual sample results are checked to fall within the range of valid standards. Results falling outside the valid range are excluded.

Table 1 presents summary statistics for the treatment and placebo groups in a study monitoring levels of IL-23, IL-7, and IP-10. Only p-values less than 0.05 are included in the table.

TABLE 1

Summary Statistics of Cytokine Biomarker Changes

| CYTO-KINE | TREATMENT GROUP | | | | PLACEBO GROUP | | | | p-value |
|---|---|---|---|---|---|---|---|---|---|
| | Visit | N | Mean | SE | Visit | N | Mean | SE | |
| IL-23 | 1 | 36 | 119.93 | 12.17 | 1 | 13 | 113.78 | 34.55 | |
| | 5 | 34 | 97.60 | 12.52 | 5 | 11 | 173.30 | 37.56 | 0.026 |
| | 13 | 32 | 107.05 | 12.91 | 13 | 13 | 149.26 | 34.55 | |

TABLE 1-continued

Summary Statistics of Cytokine Biomarker Changes

| CYTO-KINE | TREATMENT GROUP | | | | PLACEBO GROUP | | | | p-value |
|---|---|---|---|---|---|---|---|---|---|
| | Visit | N | Mean | SE | Visit | N | Mean | SE | |
| IL-7 | 1 | 16 | 1.39 | 0.14 | 1 | 7 | 1.68 | 0.48 | |
| | 5 | 23 | 1.22 | 0.11 | 5 | 7 | 1.98 | 0.48 | 0.047 |
| | 13 | 20 | 1.06 | 0.12 | 13 | 8 | 2.04 | 0.45 | 0.004 |
| IP-10 | 1 | 41 | 37.53 | 2.15 | 1 | 15 | 36.14 | 2.13 | |
| | 5 | 38 | 41.11 | 2.24 | 5 | 14 | 35.66 | 2.21 | |
| | 13 | 38 | 35.11 | 2.24 | 13 | 13 | 38.31 | 2.29 | |

In this study, when comparing the treatment and placebo groups, the biomarker concentrations tended to be higher in the placebo group relative to the treatment group at all visits, including at visit 1 when blood samples were taken prior to any injections. The p-values for the comparison of mean concentrations at each visit is reported if the difference was considered significant (p<0.05). In each case, the mean concentrations for the placebo group was greater than for the treatment group.

Figure 7A:
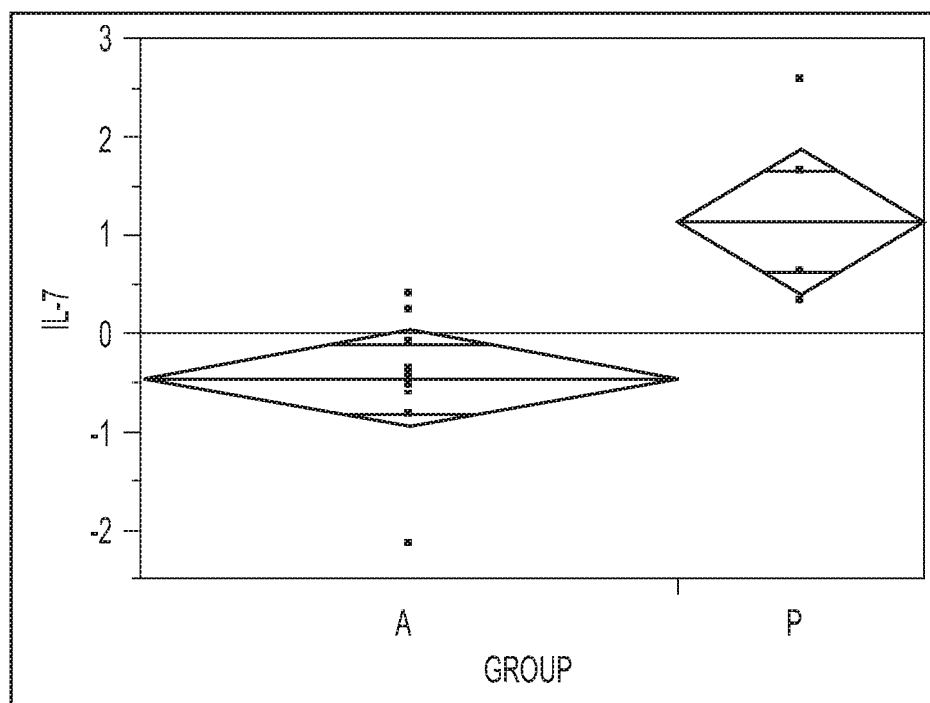
FIGS. 7A, 7B, and 7C illustrate comparison of changes in biomarker levels of IL-7, IP-10, and IL-23, respectively, within a treatment group and a placebo group in accordance with the present disclosure.
Figure 7B:
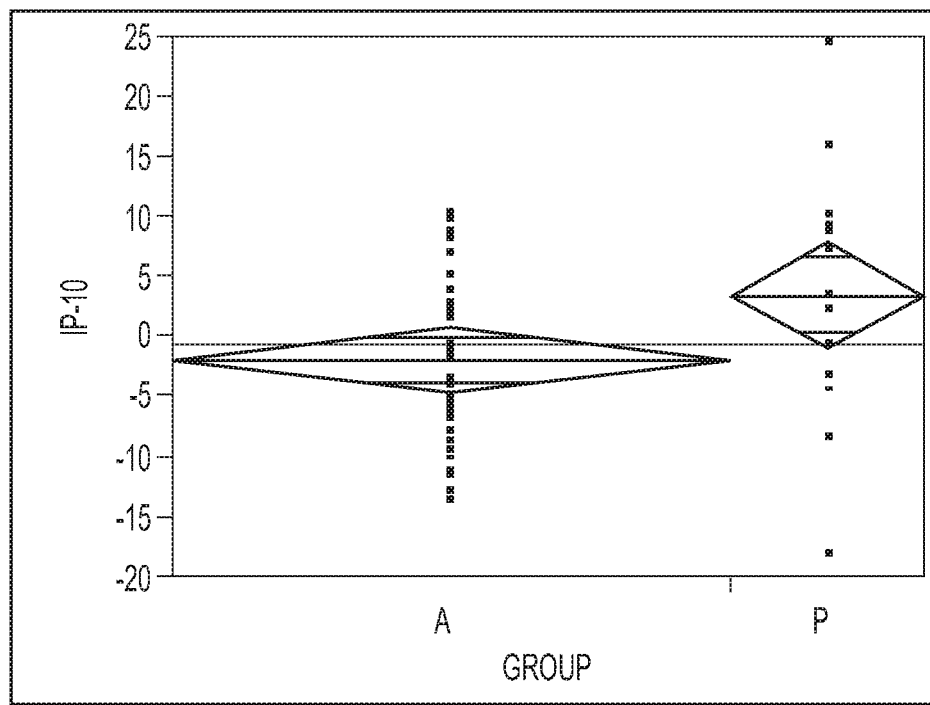
Figure 7C:
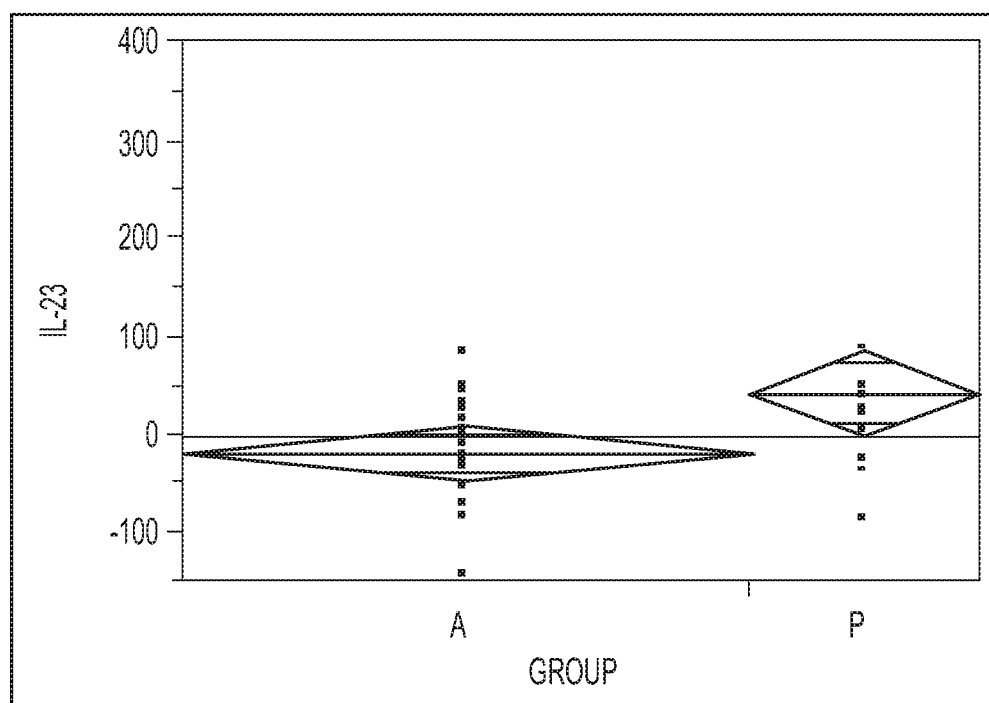

Furthermore, in this study, the change in biomarker levels with respect to baseline levels (V13-V1) were compared between the treatment groups. In general, relative decreases in biomarker levels were observed in the actively treated groups as compared to the placebo group. Three biomarkers (IL7, IP-10, and IL-23) showed statistically significant decreases after treatment when compared to the placebo group. FIGS. 7A, 7B, and 7C, illustrate comparison of changes in biomarker levels of IL-7, IP-10, and IL-23, respectively, using ANOVA one way analysis. A denotes treatment group, P denotes placebo group; change in biomarker levels are reported in terms of pg/mL.

The actively treated group is subdivided into those who showed complete resolution of all treated warts and those who showed less than 50% complete resolution. Comparison of mean changes after treatment between these two subgroups reveals a significant difference for the cytokine IL-23. The change noted in the high responder subgroup corresponds to a 35% decrease from baseline values, while the low responder subgroup exhibits a 5% decrease. In comparison, the placebo group on average exhibits a 35% increase in IL-23 concentration.

Example 6—Treatment by Injections to a Single Wart

To treat a patient between 12 to 65 year old with between 3 and 20 common warts, intralesional injections of a pharmaceutical composition of the present disclosure at a dose of 0.3 unit of potency are provided to the largest common wart every second week (14±2 days) for a maximum of 6 injections. If the primary common wart exhibits a complete response, the second largest injectable common wart of all anatomical regions is injected with the same pharmaceutical composition at the same dose of 0.3 unit of potency. If an injected wart recurs after exhibiting a complete response, it is re-injected instead of the non-primary injected wart that was injected at the previous visit. This injection strategy is repeated for a maximum of 6 injections or until all injectable common warts exhibit a complete response, if it occurs before all 6 injections are used. Complete resolution of the primary injected wart is determined one month after the last injection.

The above treatment is effective for completely resolving 66% of all primary injected warts at any number of injections, compared to 37% of those injected with a placebo. The median number of injections required to completely resolve a primary injected wart is 5 injections, compared to 10 injections of the placebo. Furthermore, at 4 months following the last injection, 46% of primary injected warts remain completely resolved, compared to 37% of those injected with a placebo.

The above treatment is also effective for resolving all common warts in 32% of the 61 subjects treated, compared to 21% of subjects receiving placebo.

From the foregoing, it will be appreciated that the present invention can be embodied in various ways, which include but not limited to the following:

Embodiment 1. A method for treating a common wart in a subject in need thereof, the method comprises administering one or more intralesional injections to the subject of an amount of a pharmaceutical composition effective for complete resolution of the common wart at a cumulative dose of 2.5 units of potency, where the pharmaceutical composition comprises a filtered extract of Candida albicans and secreted antigens.

Embodiment 2. The method of embodiment 1, where the pharmaceutical composition is further effective for reducing the diameter of the common wart by at least 50% at a cumulative dose of 1 unit of potency.

Embodiment 3. A method for treating a common wart in a subject in need thereof, the method comprises administering one or more intralesional injections to the subject of an amount of a pharmaceutical composition capable of complete resolution of the common wart at a cumulative dose of 2.5 units of potency, where the pharmaceutical composition comprises a filtered extract of Candida albicans and secreted antigens.

Embodiment 4. The method of embodiment 3, where the pharmaceutical composition is further capable of reducing the diameter of the common wart by at least 50% at a cumulative dose of 1 unit of potency.

Embodiment 5. The method of embodiment 1 or 3, where the complete resolution is identified by a lack of recurrence of the common wart at the same site observed at least 20 weeks from administration of the first intralesional injection.

Embodiment 6. The method of embodiment 1 or 3, where the complete resolution is accompanied by a lack of scarring at the location of the common wart.

Embodiment 7. The method of embodiment 1 or 3, where the complete resolution is accompanied by a low level of hypopigmentation at the location of the common wart.

Embodiment 8. The method of any one of embodiments 1-4, where the common wart measures between about 3 mm and about 20 mm before the administering.

Embodiment 9. The method of any one of embodiments 1-4, where the administering is providing an intralesional injection to the subject.

Embodiment 10. The method of embodiment 9, where the administering is providing an intralesional injection near the perimeter of the common wart.

Embodiment 11. The method of embodiment 9, where the administering is providing an intralesional injection at the perimeter of the common wart.

Embodiment 12. The method of embodiment 9, where the administering is providing an intralesional injection in the common wart.

Embodiment 13. The method of any one of embodiments 1-4, where the administering is providing two or more intralesional injections to the subject.

Embodiment 14. The method of embodiment 13, where each of the two or more intralesional injections is provided at a dose of at least 0.5 unit of potency.

Embodiment 15. The method of any one of embodiments 1-4, where the two or more intralesional injections are provided to the subject over a period of time.

Embodiment 16. The method of embodiment 15, where a pair of intralesional injections in the two or more intralesional injections are provided about two weeks apart to the subject.

Embodiment 17. The method of embodiment 15, where a pair of intralesional injections in the two or more intralesional injections are provided about three weeks apart to the subject.

Embodiment 18. The method of embodiment 15, where the two or more intralesional injections are provided to the subject over at least about 8 weeks.

Embodiment 19. The method of embodiment 13, where the two or more intralesional injections are provided in two or more subgroups of intralesional injections over a period of time.

Embodiment 20. The method of embodiment 19, where a subgroup within the two or more subgroups of intralesional injections provides a total dose of at least 0.5 unit of potency.

Embodiment 21. The method of embodiment 19 or 20, where a pair of subgroups within the two or more subgroups of intralesional injections are provided about two weeks apart to the subject.

Embodiment 22. The method of embodiment 19 or 20, where a pair of subgroups within the two or more subgroups of intralesional injections are provided about three weeks apart to the subject.

Embodiment 23. The method of embodiment 19 or 20, where the two or more subgroups of intralesional injections are provided to the subject over at least about 8 weeks.

Embodiment 24. The method of embodiment 19 or 20, where a subgroup within the two or more subgroups comprises two intralesional injections around the common wart.

Embodiment 25. The method of embodiment 19 or 20, where a subgroup within the two or more subgroups comprises three intralesional injections around the common wart.

Embodiment 26. The method of embodiment 19 or 20, where a subgroup within the two or more subgroups comprises four intralesional injections around the common wart.

Embodiment 27. The method of embodiment 19 or 20, where a subgroup within the two or more subgroups comprises five injections around the common wart.

Embodiment 28. The method of embodiment 19 or 20, where a subgroup within the two or more subgroups comprises six intralesional injections around the common wart.

Embodiment 29. The method of any one of embodiments 24-28, where the intralesional injections within the subgroup are approximately evenly spaced apart near the perimeter of the common wart.

Embodiment 30. The method of any one of embodiments 24-28, where the intralesional injections within the subgroup are approximately evenly spaced apart at the perimeter of the common wart.

Embodiment 31. The method of any one of embodiments 24-28, where the intralesional injections within the subgroup are administered at approximately the same time.

Embodiment 32. A method for treating a common wart in a subject in need thereof, the method comprises administering one or more intralesional injections to the subject of an amount of a pharmaceutical composition effective for partial resolution of the common wart at a cumulative dose of 5 units of potency, where the pharmaceutical composition comprises a filtered extract of *Candida albicans* and secreted antigens.

Embodiment 33. The method of embodiment 32, where the pharmaceutical composition is further effective for reducing the diameter of the common wart by at least 50% at a cumulative dose of 1 unit of potency.

Embodiment 34. A method for treating a common wart in a subject in need thereof, the method comprises administering one or more intralesional injections to the subject of an amount of a pharmaceutical composition capable of partial resolution of the common wart at a cumulative dose of 5 units of potency, where the pharmaceutical composition comprises a filtered extract of *Candida albicans* and secreted antigens.

Embodiment 35. The method of embodiment 34, where the pharmaceutical composition is further capable of reducing the diameter of the common wart by at least 50% at a cumulative dose of 1 unit of potency.

Embodiment 36. The method of embodiment 32 or 34, where the partial resolution is identified by a reduction in wart diameter.

Embodiment 37. The method of any one of embodiments 32-35, where the common wart measures between about 3 mm and about 20 mm before the administering.

Embodiment 38. The method of any one of embodiments 32-35, where the administering is providing an intralesional injection to the subject.

Embodiment 39. The method of embodiment 38, where the administering is providing an intralesional injection near the perimeter of the common wart.

Embodiment 40. The method of embodiment 38, where the administering is providing an intralesional injection at the perimeter of the common wart.

Embodiment 41. The method of embodiment 38, where the administering is providing an intralesional injection in the common wart.

Embodiment 42. The method of any one of embodiments 32-35, where the administering is providing two or more intralesional injections to the subject.

Embodiment 43. The method of embodiment 42, where each of the two or more intralesional injections is provided at a dose of at least 0.5 unit of potency.

Embodiment 44. The method of any one of embodiments 32-35, where the two or more intralesional injections are provided to the subject over a period of time.

Embodiment 45. The method of embodiment 44, where a pair of intralesional injections in the two or more intralesional injections are provided about two weeks apart to the subject.

Embodiment 46. The method of embodiment 44, where a pair of intralesional injections in the two or more intralesional injections are provided about three weeks apart to the subject.

Embodiment 47. The method of embodiment 44, where the two or more intralesional injections are provided to the subject over at least about 18 weeks.

Embodiment 48. The method of embodiment 42, where the two or more intralesional injections are provided in two or more subgroups of intralesional injections over a period of time.

Embodiment 49. The method of embodiment 48, where a subgroup within the two or more subgroups of intralesional injections provides a total dose of at least 0.5 unit of potency.

Embodiment 50. The method of embodiment 48 or 49, where a pair of subgroups within the two or more subgroups of intralesional injections are provided about two weeks apart to the subject.

Embodiment 51. The method of embodiment 48 or 49, where a pair of subgroups within the two or more subgroups of intralesional injections are provided about three weeks apart to the subject.

Embodiment 52. The method of embodiment 48 or 49, where the two or more subgroups of intralesional injections are provided to the subject over at least about 18 weeks.

Embodiment 53. The method of embodiment 48 or 49, where a subgroup within the two or more subgroups comprises two intralesional injections around the common wart.

Embodiment 54. The method of embodiment 48 or 49, where a subgroup within the two or more subgroups comprises three intralesional injections around the common wart.

Embodiment 55. The method of embodiment 48 or 49, where a subgroup within the two or more subgroups comprises four intralesional injections around the common wart.

Embodiment 56. The method of embodiment 48 or 49, where a subgroup within the two or more subgroups comprises five injections around the common wart.

Embodiment 57. The method of embodiment 48 or 49, where a subgroup within the two or more subgroups comprises six intralesional injections around the common wart.

Embodiment 58. The method of any one of embodiments 52-57, where the intralesional injections within the subgroup are approximately evenly spaced apart near the perimeter of the common wart.

Embodiment 59. The method of any one of embodiments 52-57, where the intralesional injections within the subgroup are approximately evenly spaced apart at the perimeter of the common wart.

Embodiment 60. The method of any one of embodiments 52-57, where the intralesional injections within the subgroup are administered at approximately the same time.

Embodiment 61. A method for treating a plurality of common warts in a subject in need thereof, the method comprises administering one or more intralesional injections to the subject of an amount of a pharmaceutical composition effective for partial resolution of the plurality of common warts at a cumulative dose of 5 units of potency, where the pharmaceutical composition comprises a filtered extract of *Candida albicans* and secreted antigens.

Embodiment 62. A method for treating a plurality of common warts in a subject in need thereof, the method comprises administering one or more intralesional injections to the subject of an amount of a pharmaceutical composition capable of partial resolution of the plurality of common warts at a cumulative dose of 5 units of potency, where the pharmaceutical composition comprises a filtered extract of *Candida albicans* and secreted antigens.

Embodiment 63. The method of embodiment 61 or 62, where the partial resolution is identified by a reduction in wart diameter.

Embodiment 64. The method of embodiment 61 or 62, where the plurality of common warts comprise 3 to 20 common warts.

Embodiment 65. The method of embodiment 61 or 62, where the plurality of common warts are located within the same anatomical location in the subject.

Embodiment 66. The method of embodiment 61 or 62, where the administering is providing an intralesional injection to the subject.

Embodiment 67. The method of embodiment 61 or 62, where the administering is providing two or more intralesional injections to the subject.

Embodiment 68. The method of embodiment 67, where the two or more intralesional injections are provided to the subject over a period of time.

Embodiment 69. The method of embodiment 68, where a pair of intralesional injections in the two or more intralesional injections are provided about two weeks apart to the subject.

Embodiment 70. The method of embodiment 68, where a pair of intralesional injections in the two or more intralesional injections are provided about three weeks apart to the subject.

Embodiment 71. The method of embodiment 68, where the two or more intralesional injections are provided to the subject over at least about 18 weeks.

Embodiment 72. The method of embodiment 67, where each of the two or more intralesional injections is provided at a dose of at least 0.5 unit of potency.

Embodiment 73. The method of embodiment 61 or 62, further comprising identifying the largest common wart within the plurality of common warts.

Embodiment 74. The method of embodiment 73, where the largest common wart measures between about 3 mm and about 20 mm before the administering.

Embodiment 75. The method of embodiment 73, where the administering is providing an intralesional injection at the perimeter of the largest common wart.

Embodiment 76. The method of embodiment 73, where the administering is providing an intralesional injection near the perimeter of the largest common wart.

Embodiment 77. The method of embodiment 73, where the administering is providing an intralesional injection in the largest common wart.

Embodiment 78. The method of embodiment 73, where the administering is providing two or more intralesional injections to the largest common wart.

Embodiment 79. The method of embodiment 78, where each of the two or more intralesional injections is provided at a dose of at least 0.5 unit of potency.

Embodiment 80. The method of embodiment 78 or 79, where the two or more intralesional injections are provided to the subject over a period of time.

Embodiment 81. The method of embodiment 80, where a pair of intralesional injections in the two or more intralesional injections are provided about two weeks apart to the subject.

Embodiment 82. The method of embodiment 80, where a pair of intralesional injections in the two or more intralesional injections are provided about three weeks apart to the subject.

Embodiment 83. The method of embodiment 80, where the two or more intralesional injections are provided to the subject over at least about 18 weeks.

Embodiment 84. The method of embodiment 78, where the two or more intralesional injections are provided in two or more subgroups of intralesional injections over a period of time.

Embodiment 85. The method of embodiment 84, where a subgroup within the two or more subgroups of intralesional injections provides a total dose of at least 0.5 unit of potency.

Embodiment 86. The method of embodiment 84 or 85, where a pair of subgroups within the two or more subgroups of intralesional injections are provided about two weeks apart to the subject.

Embodiment 87. The method of embodiment 84 or 85, where a pair of subgroups within the two or more subgroups of intralesional injections are provided about three weeks apart to the subject.

Embodiment 88. The method of embodiment 84 or 85, where the two or more subgroups of intralesional injections are provided to the subject over at least about 18 weeks.

Embodiment 89. The method of embodiment 84 or 85, where a subgroup within the two or more subgroups comprises two intralesional injections around the largest common wart.

Embodiment 90. The method of embodiment 84 or 85, where a subgroup within the two or more subgroups comprises three intralesional injections around the largest common wart.

Embodiment 91. The method of embodiment 84 or 85, where a subgroup within the two or more subgroups comprises four intralesional injections around the largest common wart.

Embodiment 92. The method of embodiment 84 or 85, where a subgroup within the two or more subgroups comprises five injections around the largest common wart.

Embodiment 93. The method of embodiment 84 or 85, where a subgroup within the two or more subgroups comprises six intralesional injections around the largest common wart.

Embodiment 94. The method of any one of embodiments 89-93, where the intralesional injections within the subgroup are approximately evenly spaced apart near the perimeter of the largest common wart.

Embodiment 95. The method of any one of embodiments 89-93, where the intralesional injections within the subgroup are approximately evenly spaced apart at the perimeter of the largest common wart.

Embodiment 96. The method of any one of embodiments 89-93, where the intralesional injections within the subgroup are administered at approximately the same time.

Embodiment 97. A method for treating a plurality of common warts in a subject in need thereof, the method comprises administering one or more intralesional injections to the subject of an amount of a pharmaceutical composition effective for reducing the diameter of each of the plurality of common warts by at least 50% at a cumulative dose of 1 unit of potency, where the pharmaceutical composition comprises a filtered extract of *Candida albicans* and secreted antigens.

Embodiment 98. A method for treating a plurality of common warts in a subject in need thereof, the method comprises administering one or more intralesional injections to the subject of an amount of a pharmaceutical composition capable of reducing the diameter of each of the plurality of common warts by at least 50% at a cumulative dose of 1 unit of potency, where the pharmaceutical composition comprises a filtered extract of *Candida albicans* and secreted antigens.

Embodiment 99. The method of embodiment 97 or 98, where the plurality of common warts comprise 3 to 20 common warts.

Embodiment 100. The method of embodiment 97 or 98, where the plurality of common warts are located within the same anatomical location in the subject.

Embodiment 101. The method of embodiment 97 or 98, where the administering is providing an intralesional injection to the subject.

Embodiment 102. The method of embodiment 97 or 98, where the administering is providing two or more intralesional injections to the subject.

Embodiment 103. The method of embodiment 102, where the two or more intralesional injections are provided to the subject over a period of time.

Embodiment 104. The method of embodiment 103, where a pair of intralesional injections in the two or more intralesional injections are provided about two weeks apart to the subject.

Embodiment 105. The method of embodiment 103, where a pair of intralesional injections in the two or more intralesional injections are provided about three weeks apart to the subject.

Embodiment 106. The method of embodiment 102, where each of the two or more intralesional injections is provided at a dose of at least 0.5 unit of potency.

Embodiment 107. The method of embodiment 97 or 98, further comprising identifying the largest common wart within the plurality of common warts.

Embodiment 108. The method of embodiment 107, where the largest common wart measures between about 3 mm and about 20 mm before the administering.

Embodiment 109. The method of embodiment 107, where the administering is providing an intralesional injection at the perimeter of the largest common wart.

Embodiment 110. The method of embodiment 107, where the administering is providing an intralesional injection near the perimeter of the largest common wart.

Embodiment 111. The method of embodiment 107, where the administering is providing an intralesional injection in the largest common wart.

Embodiment 112. The method of embodiment 107, where the administering is providing two or more intralesional injections to the largest common wart.

Embodiment 113. The method of embodiment 112, where each of the two or more intralesional injections is provided at a dose of at least 0.5 unit of potency.

Embodiment 114. The method of embodiment 112 or 113, where the two or more intralesional injections are provided to the subject over a period of time.

Embodiment 115. The method of embodiment 114, where a pair of intralesional injections in the two or more intralesional injections are provided about two weeks apart to the subject.

Embodiment 116. The method of embodiment 114, where a pair of intralesional injections in the two or more intralesional injections are provided about three weeks apart to the subject.

Embodiment 117. The method of embodiment 112, where the two or more intralesional injections are provided in two or more subgroups of intralesional injections over a period of time.

Embodiment 118. The method of embodiment 117, where each of the two or more subgroups of intralesional injections is provided at a total dose of at least 0.5 unit of potency.

Embodiment 119. The method of embodiment 117 or 118, where a pair of subgroups within the two or more subgroups of intralesional injections are provided about two weeks apart to the subject.

Embodiment 120. The method of embodiment 117 or 118, where a pair of subgroups within the two or more subgroups of intralesional injections are provided about three weeks apart to the subject.

Embodiment 121. The method of embodiment 117 or 118, where the two or more subgroups of intralesional injections are provided to the subject over at least about two weeks.

Embodiment 122. The method of embodiment 117 or 118, where a subgroup within the two or more subgroups comprises two intralesional injections around the largest common wart.

Embodiment 123. The method of embodiment 117 or 118, where a subgroup within the two or more subgroups comprises three intralesional injections around the largest common wart.

Embodiment 124. The method of embodiment 117 or 118, where a subgroup within the two or more subgroups comprises four intralesional injections around the largest common wart.

Embodiment 125. The method of embodiment 117 or 118, where a subgroup within the two or more subgroups comprises five injections around the largest common wart.

Embodiment 126. The method of embodiment 117 or 118, where a subgroup within the two or more subgroups comprises six intralesional injections around the largest common wart.

Embodiment 127. The method of any one of embodiments 122-126, where the intralesional injections within the subgroup are approximately evenly spaced apart near the perimeter of the largest common wart.

Embodiment 128. The method of any one of embodiments 122-126, where the intralesional injections within the subgroup are approximately evenly spaced apart at the perimeter of the largest common wart.

Embodiment 129. The method of any one of embodiments 122-126, where the intralesional injections within the subgroup are administered at approximately the same time.

Embodiment 130. A method for treating a non-common wart in a subject in need thereof, where the subject has one or more common warts, the method comprises administering one or more intralesional injections to the subject of an amount of a pharmaceutical composition effective for complete resolution of the non-common wart at a cumulative dose of 5 units of potency, where the pharmaceutical composition comprises a filtered extract of *Candida albicans* and secreted antigens.

Embodiment 131. A method for treating a non-common wart in a subject in need thereof, where the subject has one or more common warts, the method comprises administering one or more intralesional injections to the subject of an amount of a pharmaceutical composition capable of complete resolution of the non-common wart at a cumulative dose of 5 units of potency, where the pharmaceutical composition comprises a filtered extract of *Candida albicans* and secreted antigens.

Embodiment 132. The method of embodiment 130 or 131, where the non-common wart is a plantar wart.

Embodiment 133. The method of embodiment 130 or 131, where the non-common wart is a genital wart.

Embodiment 134. The method of embodiment 130 or 131, where the non-common wart is a facial wart.

Embodiment 135. The method of embodiment 130 or 131, where the non-common wart is a flat wart.

Embodiment 136. The method of embodiment 130 or 131, where the non-common wart is a periungual wart.

Embodiment 137. The method of embodiment 130 or 131, where the non-common wart is located within the same anatomical area as the one or more common warts.

Embodiment 138. The method of embodiment 130 or 131, where the complete resolution is identified by a lack of recurrence of the non-common wart at the same site observed at least 20 weeks from administration of the first intralesional injection.

Embodiment 139. The method of embodiment 130 or 131, where the administering is providing an intralesional injection to the subject.

Embodiment 140. The method of embodiment 130 or 131, where the administering is providing two or more intralesional injections to the subject.

Embodiment 141. The method of embodiment 140, where the two or more intralesional injections are provided to the subject over a period of time.

Embodiment 142. The method of embodiment 141, where a pair of intralesional injections in the two or more intralesional injections are provided two weeks apart to the subject.

Embodiment 143. The method of embodiment 141, where a pair of intralesional injections in the two or more intralesional injections are provided three weeks apart to the subject.

Embodiment 144. The method of embodiment 141, where the two or more intralesional injections are provided to the subject over 27 weeks.

Embodiment 145. The method of embodiment 140, where each of the two or more intralesional injections is provided at a dose of at least 0.5 unit of potency.

Embodiment 146. The method of embodiment 130 or 131, where the one or more common warts comprise 3 to 20 common warts.

Embodiment 147. The method of embodiment 130 or 131, further comprising identifying the largest common wart within the one or more common warts.

Embodiment 148. The method of embodiment 147, where the largest common wart measures between about 3 mm and about 20 mm before the administering.

Embodiment 149. The method of embodiment 147, where the administering is providing an intralesional injection at the perimeter of the largest common wart.

Embodiment 150. The method of embodiment 147, where the administering is providing an intralesional injection near the perimeter of the largest common wart.

Embodiment 151. The method of embodiment 147, where the administering is providing an intralesional injection in the largest common wart.

Embodiment 152. The method of embodiment 147, where the administering is providing two or more intralesional injections to the largest common wart.

Embodiment 153. The method of embodiment 152, where each of the two or more intralesional injections is provided at a dose of at least 0.5 unit of potency.

Embodiment 154. The method of embodiment 152 or 153, where the two or more intralesional injections are provided to the subject over a period of time.

Embodiment 155. The method of embodiment 154, where a pair of intralesional injections in the two or more intralesional injections are provided about two weeks apart to the subject.

Embodiment 156. The method of embodiment 154, where a pair of intralesional injections in the two or more intralesional injections are provided about three weeks apart to the subject.

Embodiment 157. The method of embodiment 154, where the two or more intralesional injections are provided to the subject over at least about 18 weeks.

Embodiment 158. The method of embodiment 152, where the two or more intralesional injections are provided in two or more subgroups of intralesional injections over a period of time.

Embodiment 159. The method of embodiment 158, where a subgroup within the two or more subgroups of intralesional injections is provided at a total dose of at least 0.5 unit of potency.

Embodiment 160. The method of embodiment 158 or 159, where a pair of subgroups within the two or more subgroups of intralesional injections are provided about two weeks apart to the subject.

Embodiment 161. The method of embodiment 158 or 159, where a pair of subgroups within the two or more subgroups of intralesional injections are provided about three weeks apart to the subject.

Embodiment 162. The method of embodiment 158 or 159, where the two or more subgroups of intralesional injections are provided to the subject over at least about 18 weeks.

Embodiment 163. The method of embodiment 158 or 159, where a subgroup within the two or more subgroups comprises two intralesional injections around the largest common wart.

Embodiment 164. The method of embodiment 158 or 159, where a subgroup within the two or more subgroups comprises three intralesional injections around the largest common wart.

Embodiment 165. The method of embodiment 158 or 159, where a subgroup within the two or more subgroups comprises four intralesional injections around the largest common wart.

Embodiment 166. The method of embodiment 158 or 159, where a subgroup within the two or more subgroups comprises five injections around the largest common wart.

Embodiment 167. The method of embodiment 158 or 159, where a subgroup within the two or more subgroups comprises six intralesional injections around the largest common wart.

Embodiment 168. The method of any one of embodiments 163-167, where the intralesional injections within the subgroup are approximately evenly spaced apart at the perimeter of the largest common wart.

Embodiment 169. The method of any one of embodiments 163-167, where the intralesional injections within the subgroup are approximately evenly spaced apart near the perimeter of the largest common wart.

Embodiment 170. The method of any one of embodiments 163-167, where the intralesional injections within the subgroup are administered at approximately the same time.

Embodiment 171. A method for treating a previously treated common wart in a subject in need thereof, the method comprises administering one or more intralesional injections to the subject of an amount of a pharmaceutical composition effective for complete resolution of the previously treated common wart at a cumulative dose of 5 units of potency, where the pharmaceutical composition comprises a filtered extract of *Candida albicans* and secreted antigens.

Embodiment 172. A method for treating a previously treated common wart in a subject in need thereof, the method comprises administering one or more intralesional injections to the subject of an amount of a pharmaceutical composition capable of complete resolution of the previously treated common wart at a cumulative dose of 5 units of potency, where the pharmaceutical composition comprises a filtered extract of *Candida albicans* and secreted antigens.

Embodiment 173. The method of embodiment 171 or 172, where the previously treated common wart is a common wart previously treated with cryotherapy.

Embodiment 174. The method of embodiment 173, where the previously treated common wart did not respond to the cryotherapy.

Embodiment 175. The method of embodiment 173, where the cryotherapy did not completely resolve the previously treated common wart.

Embodiment 176. The method of embodiment 171 or 172, where the previously treated common wart is a common wart previously treated with salicylic acid or a related acid.

Embodiment 177. The method of embodiment 176, where the related acid is trichloroacetic acid or bichloroacetic acid.

Embodiment 178. The method of embodiment 176, where the previously treated common wart did not respond to the salicylic acid or a related acid.

Embodiment 179. The method of embodiment 176, where the salicylic acid or a related acid did not completely resolve the previously treated common wart.

Embodiment 180. The method of embodiment 171 or 172, where the previously treated common wart is a common wart previously treated with a treatment selected from the group consisting of liquid nitrogen, carbon dioxide, cantharidin, simple occlusion, wart gel, apple cider vinegar, surgery, laser, tea tree oil, freeze wart spray, wart scraped, electrodessication, essential oils of lavender and oregano, and imiquimod.

Embodiment 181. The method of embodiment 180, where the previously treated common wart did not respond to the treatment.

Embodiment 182. The method of embodiment 180, where the treatment did not completely resolve the previously treated common wart.

Embodiment 183. The method of any one of embodiments 171-182, where the previously treated common wart measures between about 3 mm and about 20 mm before the administering.

Embodiment 184. The method of any one of embodiments 171-182, where the complete resolution is identified by a lack of recurrence of the previously treated common wart at the same site observed at least 20 weeks from administration of the first intralesional injection.

Embodiment 185. The method of any one of embodiments 171-182, where the complete resolution is accompanied by a lack of scarring at the location of the previously treated common wart.

Embodiment 186. The method of any one of embodiments 171-182, where the complete resolution is accompanied by a low level of hypopigmentation at the location of the previously treated common wart.

Embodiment 187. The method of any one of embodiments 171-182, where the administering is providing an intralesional injection to the subject.

Embodiment 188. The method of embodiment 187, where the administering is providing an intralesional injection at the perimeter of the previously treated common wart.

Embodiment 189. The method of embodiment 187, where the administering is providing an intralesional injection near the perimeter of the previously treated common wart.

Embodiment 190. The method of embodiment 187, where the administering is providing an intralesional injection in the previously treated common wart.

Embodiment 191. The method of any one of embodiments 171-182, where the administering is providing two or more intralesional injections to the subject.

Embodiment 192. The method of embodiment 191, where each of the two or more intralesional injections is provided at a dose of at least 0.5 unit of potency.

Embodiment 193. The method of embodiment 191 or 192, where the two or more intralesional injections are provided to the subject over a period of time.

Embodiment 194. The method of embodiment 193, where a pair of intralesional injections in the two or more intralesional injections are provided about two weeks apart to the subject.

Embodiment 195. The method of embodiment 193, where a pair of intralesional injections in the two or more intralesional injections are provided about three weeks apart to the subject.

Embodiment 196. The method of embodiment 193, where the two or more intralesional injections are provided to the subject over at least about 18 weeks.

Embodiment 197. The method of embodiment 191, where the two or more intralesional injections are provided in two or more subgroups of intralesional injections over a period of time.

Embodiment 198. The method of embodiment 197, where a subgroup within the two or more subgroups of intralesional injections provides a total dose of at least 0.5 unit of potency.

Embodiment 199. The method of embodiment 197 or 198, where a pair of subgroups within the two or more subgroups of intralesional injections are provided about two weeks apart to the subject.

Embodiment 200. The method of embodiment 197 or 198, where a pair of subgroups within the two or more subgroups of intralesional injections are provided about three weeks apart to the subject.

Embodiment 201. The method of embodiment 197 or 198, where the two or more subgroups of intralesional injections are provided to the subject over at least about 18 weeks.

Embodiment 202. The method of embodiment 197 or 198, where a subgroup within the two or more subgroups comprises two intralesional injections around the previously treated common wart.

Embodiment 203. The method of embodiment 197 or 198, where a subgroup within the two or more subgroups comprises three intralesional injections around the previously treated common wart.

Embodiment 204. The method of embodiment 197 or 198, where a subgroup within the two or more subgroups comprises four intralesional injections around the previously treated common wart.

Embodiment 205. The method of embodiment 197 or 198, where a subgroup within the two or more subgroups comprises five injections around the previously treated common wart.

Embodiment 206. The method of embodiment 197 or 198, where a subgroup within the two or more subgroups comprises six intralesional injections around the previously treated common wart.

Embodiment 207. The method of any one of embodiments 202-206, where the intralesional injections within the subgroup are approximately evenly spaced apart at the perimeter of the previously treated common wart.

Embodiment 208. The method of any one of embodiments 202-206, where the intralesional injections within the subgroup are approximately evenly spaced apart near the perimeter of the previously treated common wart.

Embodiment 209. The method of any one of embodiments 202-206, where the intralesional injections within the subgroup are administered at approximately the same time.

Embodiment 210. A method for delaying recurrence of a common wart in a subject in need thereof, the method comprises administering one or more intralesional injections to the subject of an amount of a pharmaceutical composition effective for delaying the reappearance of the common wart upon resolution at a cumulative dose of 2.5 units of potency, where the pharmaceutical composition comprises a filtered extract of *Candida albicans* and secreted antigens.

Embodiment 211. A method for delaying recurrence of a common wart in a subject in need thereof, the method comprises administering one or more intralesional injections to the subject of an amount of a pharmaceutical composition capable of delaying the reappearance of the common wart upon resolution at a cumulative dose of 2.5 units of potency, where the pharmaceutical composition comprises a filtered extract of *Candida albicans* and secreted antigens.

Embodiment 212. The method of embodiment 210 or 211, where the subject does not develop any new common warts within at least 16 weeks after the last injection of the one or more intralesional injections.

Embodiment 213. The method of embodiment 210 or 211, where the subject does not develop any new common warts within the same anatomical area of the common wart.

Embodiment 214. The method of embodiment 210 or 211, where the subject does not develop any new common warts within the same site of the common wart.

Embodiment 215. The method of embodiment 210 or 211, where the common wart measures between about 3 mm and about 20 mm before the administering.

Embodiment 216. The method of embodiment 210 or 211, where the administering is providing an intralesional injection to the subject.

Embodiment 217. The method of embodiment 216, where the administering is providing an intralesional injection at the perimeter of the common wart.

Embodiment 218. The method of embodiment 216, where the administering is providing an intralesional injection near the perimeter of the common wart.

Embodiment 219. The method of embodiment 216, where the administering is providing an intralesional injection in the common wart.

Embodiment 220. The method of embodiment 210 or 211, where the administering is providing two or more intralesional injections to the subject.

Embodiment 221. The method of embodiment 220, where each of the two or more intralesional injections is provided at a dose of at least 0.5 unit of potency.

Embodiment 222. The method of embodiment 220 or 221, where the two or more intralesional injections are provided to the subject over a period of time.

Embodiment 223. The method of embodiment 222, where a pair of intralesional injections in the two or more intralesional injections are provided about two weeks apart to the subject.

Embodiment 224. The method of embodiment 222, where a pair of intralesional injections in the two or more intralesional injections are provided about three weeks apart to the subject.

Embodiment 225. The method of embodiment 222, where the two or more intralesional injections are provided to the subject over at least about 8 weeks.

Embodiment 226. The method of embodiment 220, where the two or more intralesional injections are provided in two or more subgroups of intralesional injections over a period of time.

Embodiment 227. The method of embodiment 226, where a subgroup within the two or more subgroups of intralesional injections provides a total dose of at least 0.5 unit of potency.

Embodiment 228. The method of embodiment 226 or 227, where a pair of subgroups within the two or more subgroups of intralesional injections are provided about two weeks apart to the subject.

Embodiment 229. The method of embodiment 226 or 227, where a pair of subgroups within the two or more subgroups of intralesional injections are provided about three weeks apart to the subject.

Embodiment 230. The method of embodiment 226 or 227, where the two or more subgroups of intralesional injections are provided to the subject over at least about 8 weeks.

Embodiment 231. The method of embodiment 226 or 227, where a subgroup within the two or more subgroups comprises two intralesional injections around the common wart.

Embodiment 232. The method of embodiment 226 or 227, where a subgroup within the two or more subgroups comprises three intralesional injections around the common wart.

Embodiment 233. The method of embodiment 226 or 227, where a subgroup within the two or more subgroups comprises four intralesional injections around the common wart.

Embodiment 234. The method of embodiment 226 or 227, where a subgroup within the two or more subgroups comprises five injections around the common wart.

Embodiment 235. The method of embodiment 226 or 227, where a subgroup within the two or more subgroups comprises six intralesional injections around the common wart.

Embodiment 236. The method of any one of embodiments 231-235, where the intralesional injections within the subgroup are approximately evenly spaced apart at the perimeter of the common wart.

Embodiment 237. The method of any one of embodiments 231-235, where the intralesional injections within the subgroup are approximately evenly spaced apart near the perimeter of the common wart.

Embodiment 238. The method of any one of embodiments 231-235, where the intralesional injections within the subgroup are administered at approximately the same time.

Embodiment 239. The method of any one of embodiments 1-238, where the pharmaceutical composition comprises at least 80% mannose.

Embodiment 240. The method of any one of embodiments 1-239, where the pharmaceutical composition comprises at least 8% glucose.

Embodiment 241. The method of any one of embodiments 1-240, where the pharmaceutical composition comprises at least 1% galactose.

Embodiment 242. The method of any one of embodiments 1-240, where the antigens have a molecular weight of about 167 kilodaltons.

Embodiment 243. The method of any one of embodiments 1-241, where the subject is between the ages of 18 and 65.

Embodiment 244. The method of any one of embodiments 1-243, where the subject was diagnosed with a first common wart at least 12 weeks prior to receiving the one or more intralesional injections.

Embodiment 245. The method of any one of embodiments 1-244, where the subject was not diagnosed with a recalcitrant wart.

Embodiment 246. The method of any one of embodiments 1-245, where the subject has a baseline result of between 5 mm and 25 mm to the Delayed Type Hypersensitivity test.

Embodiment 247. The method of any one of embodiments 1-246, where the subject is not diagnosed with a systematic disease that compromises immune function.

Embodiment 248. The method of any one of embodiments 1-246, where the subject is not diagnosed with a localized disease that compromises immune function.

Embodiment 249. The method of any one of embodiments 1-246, where the subject is not diagnosed with a systematic condition that compromises immune function.

Embodiment 250. The method of any one of embodiments 1-246, where the subject is not diagnosed with a localized condition that compromises immune function.

Embodiment 251. The method of any one of embodiments 1-246, where the subject is not diagnosed with psoriasis.

Embodiment 252. The method of any one of embodiments 1-251, where the subject is not receiving a treatment resulting in being immunocompromised.

Embodiment 253. The method of any one of embodiments 1-252, where the subject has not been diagnosed with diabetes mellitus.

Embodiment 254. The method of any one of embodiments 1-253, where the subject does not have a history of keloid formation.

Embodiment 255. The method of any one of embodiments 1-254, where the subject does not have an existing dermatologic condition in the same anatomical area as the wart being treated.

Embodiment 256. The method of any one of embodiments 1-255, where the subject does not have an underlying inflammatory condition.

Embodiment 257. The method of embodiment 256, where the underlying inflammatory condition is an arthritic joint.

Embodiment 258. The method of any one of embodiments 1-257, where the subject has not received one or more treatments selected from the group consisting of liquid nitrogen, carbon dioxide, electrodessication, laser, surgery, simple occlusion, salicylic acid, trichloroacetic acid, bichloroacetic acid, over-the-counter treatments, and cantharidin, within 4 weeks prior to the administering.

Embodiment 259. The method of any one of embodiments 1-258, where the subject has not received one or more immunotherapy selected from the group consisting of diphenylchyclopropenone (DPCP), dinitrochlorobenzene (DNCB), imiquimod, 5-florouracil, bleomycin, and podophyllin, within 12 weeks prior to the administering.

Embodiment 260. The method of any one of embodiments 1-259, where the subject has not received one or more systematic treatment selected from the group consisting of cimetidine, zinc supplements at a dose higher than 20 mg of elemental zinc daily, azathioprine, 6-mercaptopurine, methotrexate, infliximab, adalimumab, etanercept, and steroid, within 12 weeks prior to the administering.

Embodiment 261. The method of any one of embodiments 1-260, where the subject has not received any investigational agent within 30 days prior to the administering.

Embodiment 262. The method of any one of embodiments 1-260, where the subject has not received any investigational agent within 5 half-lives of the investigational agent prior to the administering.

Embodiment 263. A medicament comprising a filtered extract of *Candida albicans* and secreted antigens formulated for complete resolution of a common wart at a cumulative dose of 2.5 units of potency.

Embodiment 264. A medicament comprising a filtered extract of *Candida albicans* and secreted antigens formulated for partial resolution of a common wart at a cumulative dose of units of potency.

Embodiment 265. A medicament comprising a filtered extract of *Candida albicans* and secreted antigens formulated for reducing the diameter of a common wart by at least 50% at a cumulative dose of 1 unit of potency.

Embodiment 266. A medicament comprising a filtered extract of *Candida albicans* and secreted antigens formulated for partial resolution of a plurality of common warts at a cumulative dose of 5 units of potency.

Embodiment 267. A medicament comprising a filtered extract of *Candida albicans* and secreted antigens formulated for reducing the diameter of a plurality of common warts by at least 50% at a cumulative dose of 1 unit of potency.

Embodiment 268. A medicament comprising a filtered extract of *Candida albicans* and secreted antigens formulated for complete resolution of a non-common wart at a cumulative dose of 5 units of potency.

Embodiment 269. A medicament comprising a filtered extract of *Candida albicans* and secreted antigens formulated for complete resolution of a previously treated common wart at a cumulative dose of 5 units of potency.

Embodiment 270. A medicament comprising a filtered extract of *Candida albicans* and secreted antigens formulated for delaying the reappearance of the common wart upon resolution at a cumulative dose of 2.5 units of potency.

Embodiment 271. The medicament of any one of embodiments 263-270, where the medicament comprises at least 80% mannose.

Embodiment 272. The medicament of any one of embodiments 263-270, where the medicament comprises at least 8% glucose.

Embodiment 273. The medicament of any one of embodiments 263-270, where the medicament comprises at least 1% galactose.

Embodiment 274. The medicament of any one of embodiments 263-270, where the antigens have a molecular weight of about 167 kilodaltons.

Embodiment 275. The medicament of any one of embodiments 263-274, where the medicament is formulated in a vial.

Embodiment 276. The medicament of embodiment 275, where the vial is a multi-dose preserved vial.

Embodiment 277. The medicament of embodiment 275, where the vial is a single-dose unpreserved vial.

Embodiment 278. The medicament of embodiment 275, where the vial is a glass vial.

Embodiment 279. The medicament of embodiment 278, where the glass vial is a 2 mL vial.

Embodiment 280. The medicament of any one of embodiments 263-273, where the medicament is formulated in a prefilled syringe.

Embodiment 281. The medicament of embodiment 280, where the prefilled syringe has a volume of 0.5 mL.

Embodiment 282. A method for reducing the level of IL-23 in a subject diagnosed with a common wart, the method comprises administering one or more intralesional injections to the subject of an amount of a pharmaceutical composition at a cumulative dose of 1 unit of potency, where the pharmaceutical composition comprises a filtered extract of *Candida albicans* and secreted antigens.

Embodiment 283. The method of embodiment 282, where the level of IL-23 in the subject is reduced for at least about 15% upon receipt of the cumulative dose when compared to a level of IL-23 measured in the subject before the administering.

Embodiment 284. A method for completely resolving a common wart in a subject in need thereof, the method comprises reducing the level of IL-23 by at least about 35% in a subject in need thereof.

Embodiment 285. The method of embodiment 284, where the reducing is achieved by administering one or more intralesional injections to the subject of an amount of a pharmaceutical composition at a cumulative dose of 3 units of potency, where the pharmaceutical composition comprises a filtered extract of *Candida albicans* and secreted antigens.

Embodiment 286. The method of embodiment 284, where the completely resolving is identified by a lack of recurrence of the common wart at the same site observed at least 20 weeks from the reducing.

Embodiment 287. A method for reducing the level of IL-7 in a subject diagnosed with a common wart, the method comprises administering one or more intralesional injections to the subject of an amount of a pharmaceutical composition at a cumulative dose of 0.6 units of potency, where the pharmaceutical composition comprises a filtered extract of *Candida albicans* and secreted antigens.

Embodiment 288. The method of embodiment 287, where the level of IL-7 in the subject is reduced for at least about 10% upon receipt of the cumulative dose when compared to a level of IL-7 measured in the subject before the administering.

Embodiment 289. A method for reducing the level of IL-7 in a subject diagnosed with a common wart, the method comprises administering one or more intralesional injections to the subject of an amount of a pharmaceutical composition at a cumulative dose of 3 units of potency, where the pharmaceutical composition comprises a filtered extract of *Candida albicans* and secreted antigens.

Embodiment 290. The method of embodiment 289, where the level of IL-7 in the subject is reduced for at least about 20% upon receipt of the cumulative dose when compared to a level of IL-7 measured in the subject before the administering.

Embodiment 291. A method for reducing the level of IP-10 in a subject diagnosed with a common wart, the method comprises administering one or more intralesional injections to the subject of an amount of a pharmaceutical composition at a cumulative dose of 3 units of potency, where the pharmaceutical composition comprises a filtered extract of *Candida albicans* and secreted antigens.

Embodiment 292. The method of embodiment 291, where the level of IP-10 in the subject is reduced for at least about 5% upon receipt of the cumulative dose when compared to a level of IP-10 measured in the subject before the administering.

Embodiment 293. The method of any one of embodiments 282, 283, and 285-292, where the administering is providing an intralesional injection to the subject.

Embodiment 294. The method of embodiment 293, where the administering is providing an intralesional injection near the perimeter of the common wart.

Embodiment 295. The method of embodiment 293, where the administering is providing an intralesional injection at the perimeter of the common wart.

Embodiment 296. The method of embodiment 293, where the administering is providing an intralesional injection in the common wart.

Embodiment 297. The method of any one of embodiments 282, 283, and 285-292, where the administering is providing two or more intralesional injections to the subject.

Embodiment 298. The method of embodiment 297, where each of the two or more intralesional injections is provided at a dose of at least 0.5 unit of potency.

Embodiment 299. The method of any one of embodiments 282, 283, and 285-292, where the two or more intralesional injections are provided to the subject over a period of time.

Embodiment 300. The method of embodiment 299, where a pair of intralesional injections in the two or more intralesional injections are provided about two weeks apart to the subject.

Embodiment 301. The method of embodiment 299, where a pair of intralesional injections in the two or more intralesional injections are provided about three weeks apart to the subject.

Embodiment 302. The method of embodiment 299, where the two or more intralesional injections are provided to the subject over at least about 8 weeks.

Embodiment 303. The method of embodiment 297, where the two or more intralesional injections are provided in two or more subgroups of intralesional injections over a period of time.

Embodiment 304. The method of embodiment 303, where a subgroup within the two or more subgroups of intralesional injections provides a total dose of at least 0.5 unit of potency.

Embodiment 305. The method of embodiment 303 or 304, where a pair of subgroups within the two or more subgroups of intralesional injections are provided about two weeks apart to the subject.

Embodiment 306. The method of embodiment 303 or 304, where a pair of subgroups within the two or more subgroups of intralesional injections are provided about three weeks apart to the subject.

Embodiment 307. The method of embodiment 303 or 304, where the two or more subgroups of intralesional injections are provided to the subject over at least about 8 weeks.

Embodiment 308. The method of embodiment 303 or 304, where a subgroup within the two or more subgroups comprises two intralesional injections around the common wart.

Embodiment 309. The method of embodiment 303 or 304, where a subgroup within the two or more subgroups comprises three intralesional injections around the common wart.

Embodiment 310. The method of embodiment 303 or 304, where a subgroup within the two or more subgroups comprises four intralesional injections around the common wart.

Embodiment 311. The method of embodiment 303 or 304, where a subgroup within the two or more subgroups comprises five injections around the common wart.

Embodiment 312. The method of embodiment 303 or 304, where a subgroup within the two or more subgroups comprises six intralesional injections around the common wart.

Embodiment 313. The method of any one of embodiments 308-312, where the intralesional injections within the subgroup are approximately evenly spaced apart near the perimeter of the common wart.

Embodiment 314. The method of any one of embodiments 308-312, where the intralesional injections within the subgroup are approximately evenly spaced apart at the perimeter of the common wart.

Embodiment 315. The method of any one of embodiments 308-312, where the intralesional injections within the subgroup are administered at approximately the same time.

Embodiment 316. The method of any one of embodiments 1-262 and 282-315, where the pharmaceutical composition comprises filtered extract of two strains of *Candida albicans* and secreted antigens.

Embodiment 317. The method of embodiment 316, where a representative sample of a first strain of the two strains of *Candida albicans* has been deposited with the ATCC under ATCC Accession No. PTA-126019.

Embodiment 318. The method of embodiment 316, where a representative sample of a first strain of the two strains of *Candida albicans* has been deposited with the ATCC under ATCC Accession No. ATCC-10231.

Embodiment 319. The method of any one of embodiments 316-318, where a representative sample of a second strain of the two strains of *Candida albicans* has been deposited with the ATCC under ATCC Accession No. PTA-126020.

Embodiment 320. The medicament of any one of embodiments 263-281, where said filtered extract of *Candida albicans* comprises two strains of *Candida albicans*.

Embodiment 321. The medicament of embodiment 320, where a representative sample of a first strain of the two strains of *Candida albicans* has been deposited with the ATCC under ATCC Accession No. PTA-126019.

Embodiment 322. The medicament of embodiment 320, where a representative sample of a first strain of the two strains of *Candida albicans* has been deposited with the ATCC under ATCC Accession No. ATCC-10231.

Embodiment 323. The medicament of any one of embodiments 320-322, where a representative sample of a second strain of the two strains of *Candida albicans* has been deposited with the ATCC under ATCC Accession No. PTA-126020.

While the present disclosure has been described with reference to particular embodiments, it will be understood by those skilled in the art that various changes may be made and equivalents may be substituted for elements thereof to adapt to particular situations without departing from the scope of the present disclosure. Therefore, it is intended that the present disclosure not be limited to the particular embodiments disclosed as the best mode contemplated for carrying out the present disclosure, but that the present disclosure will include all embodiments falling within the scope and spirit of the appended claims.

The invention claimed is:

1. A pharmaceutical composition having a cumulative dose of between 0.5 to 10 units of potency comprising a sterile filtered extract of two or more strains of *Candida albicans* and secreted antigens and a pharmaceutically acceptable diluent, wherein each of the two or more strains of *Candida albicans* is selected from the group consisting of a strain having been deposited with the American Type Culture Collection (ATCC) under ATCC Accession No. PTA-126019, a strain having been deposited under ATCC Accession No. PTA-126020, and a strain having been deposited under ATCC Accession No. ATCC-10231, and wherein the pharmaceutical composition is effective for partial or complete resolution of one or more warts.

2. The pharmaceutical composition of claim 1, wherein the pharmaceutical composition has a cumulative dose of between 1 to 5 units of potency.

3. The pharmaceutical composition of claim 1, wherein the one or more warts is a common wart.

4. The pharmaceutical composition of claim 3, wherein the pharmaceutical composition has a cumulative dose of about 2.5 units of potency.

5. The pharmaceutical composition of claim 3, wherein the pharmaceutical composition has a cumulative dose of about 5 units of potency.

6. The pharmaceutical composition of claim 1, wherein the one or more warts is a plurality of common warts.

7. The pharmaceutical composition of claim 6, wherein the pharmaceutical composition has a cumulative dose of about 5 units of potency.

8. The pharmaceutical composition of claim 6, wherein the pharmaceutical composition has a cumulative dose of about 1 unit of potency.

9. The pharmaceutical composition of claim 1, wherein the at least one wart is a non-common wart.

10. The pharmaceutical composition of claim 9, wherein the pharmaceutical composition has a cumulative dose of about 5 units of potency.

11. The pharmaceutical composition of claim 1, wherein the at least one wart is a previously treated common wart.

12. The pharmaceutical composition of claim 11, wherein the pharmaceutical composition has a cumulative dose of about 5 units of potency.

13. The pharmaceutical composition of claim 11 wherein the pharmaceutical composition has a cumulative dose of about 2.5 units of potency.

14. The pharmaceutical composition of claim 1, wherein the pharmaceutical composition comprises a first strain having been deposited under ATCC Accession No. PTA-126019, and a second strain having been deposited under ATCC Accession No. PTA-126020.

15. The pharmaceutical composition of claim 1, wherein the pharmaceutical composition comprises a first strain having been deposited under ATCC Accession No. ATCC-10231, and a second strain having been deposited under ATCC Accession No. PTA-126020.

16. The pharmaceutical composition of claim 1, wherein the pharmaceutical composition further comprises at least 80% mannose.

17. The pharmaceutical composition of claim 1, wherein the pharmaceutical composition further comprises at least 8% glucose.

18. The pharmaceutical composition of claim 1, wherein the pharmaceutical composition further comprises at least 1% galactose.

19. The pharmaceutical composition of claim 1, wherein the pharmaceutically acceptable diluent comprises
   i. 0.5% sodium chloride (NaCl),
   ii. 0.25% sodium bicarbonate ($NaHCO_3$),
   iii. 0.4% phenol,
   iv. 0.03% human serum albumin, and
   v. 8 parts per million (ppm) polysorbate 80.

20. The pharmaceutical composition of claim 1, wherein the pharmaceutical composition is injectable.

* * * * *